US009803247B2

(12) United States Patent
Rosenfeld et al.

(10) Patent No.: US 9,803,247 B2
(45) Date of Patent: Oct. 31, 2017

(54) MICRORNAS EXPRESSION SIGNATURE FOR DETERMINATION OF TUMORS ORIGIN

(71) Applicants: Rosetta Genomics Ltd., Rehovot (IL); Tel Hashomer Medical Research Infrastructure and Services Ltd., Ramat Gan (IL)

(72) Inventors: Nitzan Rosenfeld, Rehovot (IL); Shai Rosenwald, Nes Ziona (IL); Iris Barshack, Tel Aviv (IL); Dvora Nass, Karney Shomron (IL)

(73) Assignees: Rosetta Genomics, Ltd., Rehovot (IL); Tel Hashomer Medical Infrastructure and Services Ltd., Ramat Gan (IL)

(*) Notice: Subject to any disclaimer, the term of this patent is extended or adjusted under 35 U.S.C. 154(b) by 0 days.

(21) Appl. No.: 14/284,256

(22) Filed: May 21, 2014

(65) Prior Publication Data
US 2016/0115546 A1 Apr. 28, 2016

Related U.S. Application Data

(63) Continuation of application No. 12/782,067, filed on May 18, 2010, now abandoned, which is a continuation-in-part of application No. PCT/IL2008/001525, filed on Nov. 20, 2008, said application No. 12/782,067 is a continuation-in-part of application No. 12/532,940, filed as application No. PCT/IL2008/000396 on Mar. 20, 2008, now abandoned.

(60) Provisional application No. 60/989,458, filed on Nov. 21, 2007, provisional application No. 61/043,407, filed on Apr. 9, 2008, provisional application No. 61/073,774, filed on Jun. 19, 2008, provisional application No. 60/907,266, filed on Mar. 27, 2007, provisional application No. 60/929,244, filed on Jun. 19, 2007, provisional application No. 61/024,565, filed on Jan. 30, 2008.

(51) Int. Cl.
C12Q 1/68 (2006.01)

(52) U.S. Cl.
CPC ...... *C12Q 1/6886* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 5,034,506 A | 7/1991 | Summerton et al. |
| 5,235,033 A | 8/1993 | Summerton et al. |
| 6,506,559 B1 | 1/2003 | Driver et al. |
| 7,745,608 B2 | 6/2010 | Manoharan et al. |
| 2003/0134299 A1* | 7/2003 | Hogan ............... C12Q 1/6837 435/6.11 |
| 2003/0225526 A1 | 12/2003 | Golub et al. |
| 2005/0182005 A1 | 8/2005 | Tuschl et al. |
| 2007/0065844 A1 | 3/2007 | Golub et al. |
| 2007/0161004 A1* | 7/2007 | Brown ............... C12N 15/111 435/6.14 |
| 2008/0269072 A1 | 10/2008 | Hart et al. |
| 2008/0306018 A1 | 12/2008 | Croce et al. |
| 2009/0176723 A1* | 7/2009 | Brown ............... C12N 15/111 514/44 R |

FOREIGN PATENT DOCUMENTS

| EP | 1777301 A2 | 4/2007 |
| WO | WO 2005/118806 A2 | 12/2005 |
| WO | WO 2006/081284 A2 | 8/2006 |
| WO | WO 2008/029295 A2 | 3/2008 |

OTHER PUBLICATIONS

Bartel D.P., MicroRNAs: Genomics, Biogenesis, Mechanism, and Function, Cell, Jan. 2004, pp. 281-296, vol. 116.
Bartel et al. "MicroRNAs: At the Root of Plant Development?," Plant Physiology, Jun. 2003, pp. 709-717, vol. 132.
Brennecke et al., "Principles of MicroRNA-Target Recognition," PLoS Biology, Mar. 2005, pp. 0001-0015, vol. 3, No. 3, e85.
International Search Report and Written Opinion received in the corresponding International Patent Application PCT/IL2008/001525, dated May 26, 2009.
Doench et al., "Specificity of microRNA target selection in translational repression," Genes & Development, 2004, pp. 1-8.
He et al., "The role of microRNA genes in papillary thyroid carcinoma," PNAS, Dec. 2005, pp. 19075-19080, vol. 102, No. 52.
Hofacker et al., "Fast Folding and Comparison of RNA Secondary Structures (The Vienna RNA Package)," Chemical Monthly, 1994, pp. 1-34, vol. 125: 167-188.
Jay et al., "miRNA Profiling for Diagnosis and Prognosis of Human Cancer," DNA and Cell Biology, 2007, pp. 293-300, vol. 26, No. 5.
Jukic, et al., "Microrna profiling analysis of differences between the melanoma of young adults and older adults", *Journal of Translational Medicine*, 2010, vol. 8, No. 27, pp. 1-23.
Krek et al., "Combinatorial microRNA target predictions," Nature Genetics [Advanced Online Publication http://www.nature.com/naturegenetics], 2005, pp. 1-6.
Krützfeldt et al., "Silencing of microRNAs in vivo with 'antagomirs,'" Nature, 2005, pp. 1-5.
Ladeiro et al., "MicroRNA Profiling in Hepatocellular Tumors is Associated with Clinical Features and Oncogene/Tumor Suppressor Gene Mutations," Hepatology, May 2008, pp. 1-9, vol. 47, No. 5.
Leidinger, et al., "High-throughput miRNA profiling of human melanoma blood samples", *BMC Cancer*, 2010, vol. 10: 262, pp. 1-11.

(Continued)

Primary Examiner — James Martinell
(74) Attorney, Agent, or Firm — Polsinelli PC; Ron Galant

(57) ABSTRACT

The present invention provides a process for classification of specific cancers and tumors origin through the analysis of the expression patterns of specific microRNAs and nucleic acid molecules relating thereto. Classification according to a microRNA expression framework allows optimization of treatment, and determination of specific therapy.

8 Claims, 12 Drawing Sheets

(56) References Cited

OTHER PUBLICATIONS

Lewis et al., "Conserved Seed Pairing, Often Flanked by Adenosines, Indicates that Thousands of Human Genes are MicroRNA Targets," Cell, Jan. 2005, pp. 15-20, vol. 120.

Lu et al., "MicroRNA expression profiles classify human cancers," Nature, Jun. 2005, pp. 834-838, vol. 435.

MIR associated with Melanoma, Sep. 2011.

miR200c miRNAMap (hereinafter "Map"; 2005).

MIR-509 Results, Sep. 2011.

Notterman et al, "Tumor Biology and Microarray Analysis of Solid Tumors: Colorectal Cancer as a Model System," Microarrays and Cancer Research, 2002, pp. 81-111.

Rosenfeld et al., "MicroRNAs accurately identify cancer tissue origin," Nature Biotechnology [Advance Online Publication http://www.nature.com/naturebiotechnology], pp. 1-8, Mar. 23, 2008.

Shedden, et al., "Accurate Molecular Classification of Human Cancers Based on Gene Expression Using a Simple Classifier with a Pathological Tree-Based Framework", American Journal of Pathology, vol. 163, No. 5, Nov. 2003.

Shi et al., "Facile means for quantifying microRNA expression by real-time PCR," BioTechniques, 2005, pp. 519-524, vol. 39, No. 4.

Soutschek et al., "Therapeutic silencing of an endogenous gene by systemic administration of modified siRNAs," Nature, Nov. 2004, pp. 173-178, vol. 432.

Strausberg et al, "Reading the Molecular Signatures of Cancer," Microarrays and Cancer Research, 2002, 8 pgs.

Volinia et al., "A microRNA expression signature of human solid tumors defines cancer gene targets," PNAS, Feb. 2006, pp. 2257-2261, vol. 103, No. 7.

Wiemer, et al, XP-001538067, Proceedings of the American Association for Cancer Research, Apr. 2006, vol. 47, 2 pages.

Xi, et al., "Prognostic Values of microRNAs in Colorectal Cancer", Biomarker Insights, vol. 1, pp. 113-121, published online Feb. 7, 2007, pp. 113-121.

Yekta et al., "MicroRNA-Directed Cleavage of HOXB8 mRNA," Science, Apr. 2004, pp. 594-596, vol. 304.

\* cited by examiner

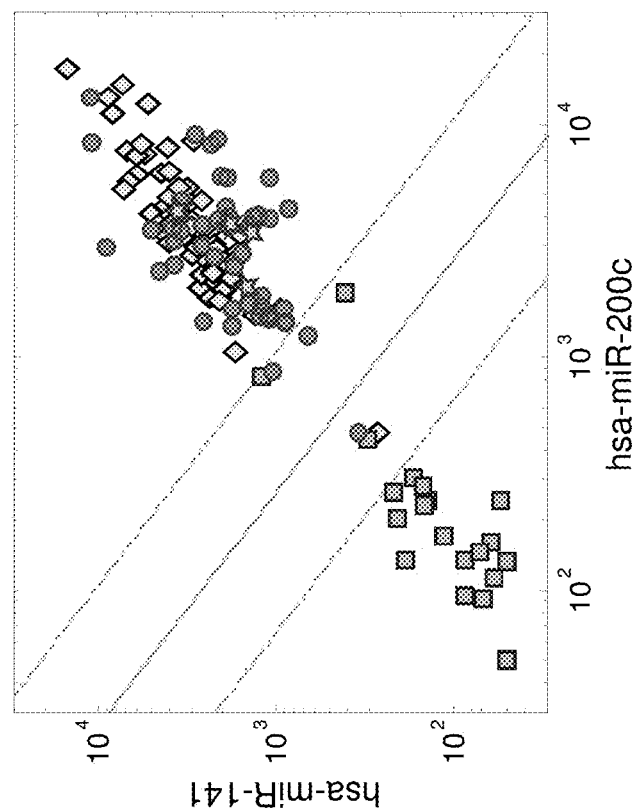
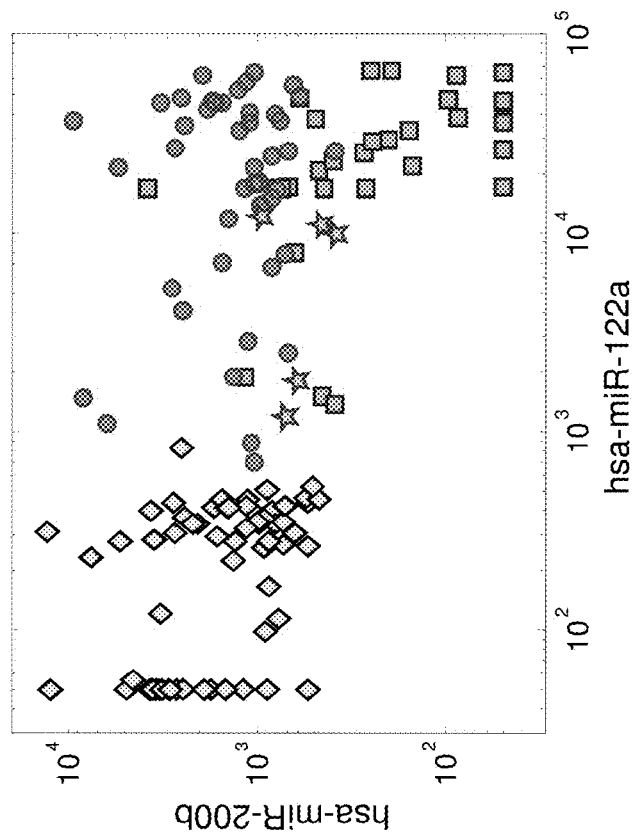
FIG. 1B
FIG. 1A

SEQUENCE LISTING

<160> NUMBER OF SEQ ID NOS: 44

<210> SEQ ID NO 1
<211> LENGTH: 22
<212> TYPE: RNA

```
<213> ORGANISM: Homo sapiens

<400> SEQUENCE: 1
uguaacagca acuccaugug ga                                           22

<210> SEQ ID NO 2
<211> LENGTH: 85
<212> TYPE: RNA
<213> ORGANISM: Homo sapiens

<400> SEQUENCE: 2
augguguuau caaguguaac agcaacucca ugggacugu guaccaauuu ccaguggaga    60
ugcuguuacu uuugaugguu accaa                                        85

<210> SEQ ID NO 3
<211> LENGTH: 88
<212> TYPE: RNA
<213> ORGANISM: Homo sapiens

<400> SEQUENCE: 3
auugguuccc gcccccugua acagcaacuc cauguggaag ugcccacugg uuccaguggg   60
gcugcuguua ucugggcga gggccagu                                      88

<210> SEQ ID NO 4
<211> LENGTH: 22
<212> TYPE: RNA
<213> ORGANISM: Homo sapiens

<400> SEQUENCE: 4
uccuucauuc caccggaguc ug                                           22

<210> SEQ ID NO 5
<211> LENGTH: 110
<212> TYPE: RNA
<213> ORGANISM: Homo sapiens

<400> SEQUENCE: 5
aaagauccuc agacaaucca ugugcuucuc uugucccuca uuccaccgga gucugucuca   60
uacccaacca gauuucagug gagugaaguu caggaggcau ggagcugaca              110

<210> SEQ ID NO 6
<211> LENGTH: 22
<212> TYPE: RNA
<213> ORGANISM: Homo sapiens

<400> SEQUENCE: 6
uaacacuguc ugguaaagau gg                                           22

<210> SEQ ID NO 7
<211> LENGTH: 104
<212> TYPE: RNA
<213> ORGANISM: Homo sapiens

<400> SEQUENCE: 7
gucggccggc ccuggguca ucuuccagua caguguugga uggucuaauu gugaagcucc    60
uaacacuguc ugguaaagau ggcucccggg ugggguucucu cggc                  104

<210> SEQ ID NO 8
<211> LENGTH: 23
<212> TYPE: RNA
<213> ORGANISM: Homo sapiens
```

```
<400> SEQUENCE: 8
uaauacugcc ggguaaugau gga                                          23

<210> SEQ ID NO 9
<211> LENGTH: 86
<212> TYPE: RNA
<213> ORGANISM: Homo sapiens

<400> SEQUENCE: 9 gggcggggc ccucgucuua cccagcagug uuugggugcg guugggaguc ucuaauacug   60
ccggguaaug auggagggccc cugucc                                     86

<210> SEQ ID NO 10
<211> LENGTH: 22
<212> TYPE: RNA
<213> ORGANISM: Homo sapiens

<400> SEQUENCE: 10
uaacacuguc ugguaacgau gu                                          22

<210> SEQ ID NO 11
<211> LENGTH: 90
<212> TYPE: RNA
<213> ORGANISM: Homo sapiens

<400> SEQUENCE: 11
ccgggccccu gugagcaucu uaccggacag ugcuggauuu cccagcuuga cucuaacacu  60
gucugguaac gauguucaaa ggugacccgc                                  90

<210> SEQ ID NO 12
<211> LENGTH: 22
<212> TYPE: RNA
<213> ORGANISM: Homo sapiens

<400> SEQUENCE: 12
uaauacugcc ugguaaugau ga                                          22

<210> SEQ ID NO 13
<211> LENGTH: 95
<212> TYPE: RNA
<213> ORGANISM: Homo sapiens

<400> SEQUENCE: 13
ccagcucggg cagccguggc caucuuacug ggcagcauug gauggaguca ggucucuaau  60
acugccuggu aaugaugacg gcggagcccu gcacg                            95

<210> SEQ ID NO 14
<211> LENGTH: 22
<212> TYPE: RNA
<213> ORGANISM: Homo sapiens

<400> SEQUENCE: 14
uauugcacuc gucccggccu cc                                          22

<210> SEQ ID NO 15
<211> LENGTH: 96
<212> TYPE: RNA
<213> ORGANISM: Homo sapiens

<400> SEQUENCE: 15
```
cgggccccgg gcgggcggga gggacgggac gcggugcagu guuguuuuuu cccccgccaa     60
uauugcacuc gucccggccu ccggccccccc cggccc                              96

<210> SEQ ID NO 16
<211> LENGTH: 22
<212> TYPE: RNA
<213> ORGANISM: Homo sapiens

<400> SEQUENCE: 16
uuaaggcacg cggugaaugc ca                                              22

<210> SEQ ID NO 17
<211> LENGTH: 83
<212> TYPE: RNA
<213> ORGANISM: Homo sapiens

<400> SEQUENCE: 17
ggccucucuc uccguguuca cagcggaccu ugauuuaaau guccauacaa uuaaggcacg     60
cggugaaugc caagaauggg gcu                                             83

<210> SEQ ID NO 18
<211> LENGTH: 117
<212> TYPE: RNA
<213> ORGANISM: Homo sapiens

<400> SEQUENCE: 18
uccggaucaa gauuagaggc ucugcucucc guguucacag cggaccuuga uuuaaugauca    60 uacaauuaag gcacgcggug aaugccaaga gcggagccua cggcugcacu ugaagga       117

<210> SEQ ID NO 19
<211> LENGTH: 68
<212> TYPE: RNA
<213> ORGANISM: Homo sapiens

<400> SEQUENCE: 19
cucugcgugu ucacagcgga ccuugauuua augucuauac aauuaaggca cgcggugaau     60
gccaagag                                                              68

<210> SEQ ID NO 20
<211> LENGTH: 22
<212> TYPE: RNA
<213> ORGANISM: Homo sapiens

<400> SEQUENCE: 20
auaaagcuag auaaccgaaa gu                                              22

<210> SEQ ID NO 21
<211> LENGTH: 89
<212> TYPE: RNA
<213> ORGANISM: Homo sapiens

<400> SEQUENCE: 21 cggggrluggu uguuaucuuu gguuaucuag cuguaugagu ggguguggagu cuucauaaag   60 cuagauaacc gaaaguaaaa auaacccca                                       89

<210> SEQ ID NO 22
<211> LENGTH: 87
<212> TYPE: RNA
<213> ORGANISM: Homo sapiens

<400> SEQUENCE: 22
ggaagcgagu uguuaucuuu gguuaucuag cuguaugagu guauggucu ucauaaagcu    60 agauaaccga aaguaaaaac uccuuca                                       87

<210> SEQ ID NO 23
<211> LENGTH: 90
<212> TYPE: RNA
<213> ORGANISM: Homo sapiens

<400> SEQUENCE: 23
ggaggcccgu uucucucuuu gguuaucuag cuguaugagu gccacagagc cgucauaaag    60
cuagauaacc gaaaguagaa augauucuca                                    90

<210> SEQ ID NO 24
<211> LENGTH: 21
<212> TYPE: RNA
<213> ORGANISM: Homo sapiens

<400> SEQUENCE: 24
ugauugucca aacgcaauuc u                                             21

<210> SEQ ID NO 25
<211> LENGTH: 159
<212> TYPE: RNA
<213> ORGANISM: Homo sapiens

<400> SEQUENCE: 25
cucccgugcg ccucccuccc uucccgcccc cgggccgcgg cuccugauug uccaaacgca    60
auucucgagu cuauggcucc ggccgagagu ugagucugga cgucccgagc cgccgccccc   120
aaaccucgag cgggagagcg ggucggaggg ucugggag                           159

<210> SEQ ID NO 26
<211> LENGTH: 89
<212> TYPE: RNA
<213> ORGANISM: Homo sapiens

<400> SEQUENCE: 26
ggggcuucgc cacugauugu ccaaacgcaa uucuuguacg agucugcggc caaccgagaa    60
uuguggcugg acaucugugg cugagcucc                                     89

<210> SEQ ID NO 27
<211> LENGTH: 23
<212> TYPE: RNA
<213> ORGANISM: Homo sapiens

<400> SEQUENCE: 27
ucuuugguua ucuagcugua uga                                           23

<210> SEQ ID NO 28
<211> LENGTH: 22
<212> TYPE: RNA
<213> ORGANISM: Homo sapiens

<400> SEQUENCE: 28
ucacagugaa ccggucucuu uu                                            22

<210> SEQ ID NO 29
<211> LENGTH: 82
<212> TYPE: RNA
<213> ORGANISM: Homo sapiens

```
<400> SEQUENCE: 29
ugagcuguug gauucggggc cguagcacug ucugagaggu uuacauuucu cacagugaac    60
cggucucuuu uucagcugcu uc                                            82

<210> SEQ ID NO 30
<211> LENGTH: 22
<212> TYPE: RNA
<213> ORGANISM: Homo sapiens

<400> SEQUENCE: 30
ucacagugaa ccggucucuu uc                                            22

<210> SEQ ID NO 31
<211> LENGTH: 84
<212> TYPE: RNA
<213> ORGANISM: Homo sapiens

<400> SEQUENCE: 31
ugugcagugg gaaggggggc cgauacacug uacgagagug aguagcaggu cucacaguga    60
accggucucu uucccuacug uguc                                          84

<210> SEQ ID NO 32
<211> LENGTH: 23
<212> TYPE: RNA
<213> ORGANISM: Homo sapiens

<400> SEQUENCE: 32
uggaguguga caauggguguu ugu                                          23

<210> SEQ ID NO 33
<211> LENGTH: 85
<212> TYPE: RNA
<213> ORGANISM: Homo sapiens

<400> SEQUENCE: 33
ccuuagcaga gcuguggagu gugacaaugg uguuugeguc uaaacuauca aacgccauua    60
ucacacuaaa uagcuacugc uaggc                                         85

<210> SEQ ID NO 34
<211> LENGTH: 28
<212> TYPE: DNA
<213> ORGANISM: Artificial Sequence
<220> FEATURE:
<223> OTHER INFORMATION: Synthetic

<400> SEQUENCE: 34
cagtcatttg gctaaggcac gcggtgaa                                      28

<210> SEQ ID NO 35
<211> LENGTH: 28
<212> TYPE: DNA
<213> ORGANISM: Artificial Sequence
<220> FEATURE:
<223> OTHER INFORMATION: Synthetic

<400> SEQUENCE: 35
cagtcatttg gctctttggt tatctagc                                      28

<210> SEQ ID NO 36
<211> LENGTH: 28
<212> TYPE: DNA
<213> ORGANISM: Artificial Sequence
```

```
<220> FEATURE:
<223> OTHER INFORMATION: Synthetic

<400> SEQUENCE: 36
cagtcatttg gcataaagct agataacc                                          28

<210> SEQ ID NO 37
<211> LENGTH: 28
<212> TYPE: DNA
<213> ORGANISM: Artificial Sequence
<220> FEATURE:
<223> OTHER INFORMATION: Synthetic

<400> SEQUENCE: 37
cagtcatttg ggtattgcac tcgtcccg                                          28

<210> SEQ ID NO 38
<211> LENGTH: 21
<212> TYPE: DNA
<213> ORGANISM: Artificial Sequence
<220> FEATURE:
<223> OTHER INFORMATION: Synthetic

<400> SEQUENCE: 38
gcaaggatga cacgcaaatt c                                                 21

<210> SEQ ID NO 39
<211> LENGTH: 23
<212> TYPE: DNA
<213> ORGANISM: Artificial Sequence
<220> FEATURE:
<223> OTHER INFORMATION: Synthetic

<400> SEQUENCE: 39
ccgttttttt tttttggcat tca                                               23

<210> SEQ ID NO 40
<211> LENGTH: 23
<212> TYPE: DNA
<213> ORGANISM: Artificial Sequence
<220> FEATURE:
<223> OTHER INFORMATION: Synthetic

<400> SEQUENCE: 40
ccgttttttt tttttcatac agc                                               23

<210> SEQ ID NO 41
<211> LENGTH: 23
<212> TYPE: DNA
<213> ORGANISM: Artificial Sequence
<220> FEATURE:
<223> OTHER INFORMATION: Synthetic

<400> SEQUENCE: 41
ccgttttttt tttttacttt cgg                                               23

<210> SEQ ID NO 42
<211> LENGTH: 22
<212> TYPE: DNA
<213> ORGANISM: Artificial Sequence
<220> FEATURE:
<223> OTHER INFORMATION: Synthetic

<400> SEQUENCE: 42 cgttttttttt ttttggaggc cg                                               22
```

```
<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
aatatggaac gcttcacg                                              18

<210> SEQ ID NO 44
<211> LENGTH: 22
<212> TYPE: DNA
<213> ORGANISM: Artificial Sequence
<220> FEATURE:
<223> OTHER INFORMATION: Synthetic

<400> SEQUENCE: 44
gcgagcacag aattaatacg ac                                         22
```

MICRORNAS EXPRESSION SIGNATURE FOR DETERMINATION OF TUMORS ORIGIN

FIELD OF THE INVENTION

The present invention relates to methods for classification of cancers and tumors origin. Specifically the invention relates to microRNA molecules associated with specific cancer, as well as various nucleic acid molecules relating thereto or derived therefrom.

BACKGROUND OF THE INVENTION microRNAs (miRs, miRNAs) are a family of 18-24 nucleotide long non-coding small RNAs, that suppress translation of target genes by binding to their mRNA, thereby regulating the expression of at least 30% of all human genes. There are currently about 850 known human microRNAs. Though highly conserved throughout evolution, a significant proportion of them is primate specific. microRNAs association with cancer has been demonstrated and several microRNAs have already been identified as oncogenes and tumor suppressors (He, H., et al., Proc Natl Acad Sci USA, 2005. 102(52): p. 19075-80).

One of the major characteristics of microRNAs is their marked tissue specificity. Many of them also exhibit temporal patterns of expression, suggesting that they play a critical role in specific tissues and in organ development, function and maintenance.

The differential diagnosis of hepatic lesions that include primary liver tumor and metastatic tumors is a frequent challenge in modern surgical pathology. Hepatic malignancies are often found in patients with advanced metastatic cancer. Identifying the origin of these tumors as well as differentiating liver metastases from primary hepatocellular carcinoma (HCC) is frequently required and poses a significant challenge that requires clinical-radiological correlation on top of careful pathological evaluation. Thorough examination assisted by a panel of immunostains is required for the identification of the origin of metastases. Extensive work-up using modern pathological tools (immunohistochemistry, electron microscopy and molecular diagnosis) and advanced imaging technology (computed tomography (CT), mammography and positron emission tomography (PET)) have resulted in some improvements in diagnosis. However, the primary site remains unknown in many patients, even on autopsy. The appropriate management of such patients is unclear and there is a high variability in clinical approaches, accompanied by poor prognosis in most cases.

The pathological characterization of brain malignancies remains a diagnostic challenge. Despite the advent of various high throughput genomic level technologies, which allow multiple DNA sequences, mRNAs or proteins to be evaluated simultaneously and systematically, these have had little impact on clinical procedures.

Differentiation between primary and metastatic tumors in the brain is often encountered in pathological practice, since metastatic tumors to the brain are quite frequent. The most common tumors to metastasize to the brain originate in the lung, breast and skin (melanomas); their respective contributions to all central nervous system (CNS) metastases are 30%, 20% and 10%. Although rare, choriocarcinoma disseminates to the brain with a particularly high frequency. In autopsy studies, 24% of cancer patients exhibited metastatic tumors in the CNS. Indeed, surgical pathologists are regularly presented with specimens from patients with a history of systemic neoplasia but with findings that suggest a primary intracranial tumor.

Therefore, there is a need for efficient and effective methods for the differentiation between primary and metastatic tumors.

SUMMARY OF THE INVENTION

The present invention provides specific nucleic acid sequences that are used for the identification, classification and diagnosis of cancers and tumor origin. The nucleic acid sequences can also be used for the differentiation between primary and metastatic tumors based on the expression pattern of a biological sample.

According to one aspect, the present invention provides a method of classifying a specific cancer, the method comprising: obtaining a biological sample from a subject; determining an expression profile of a nucleic acid sequence selected from the group consisting of SEQ ID NOS: 1-33, a fragment thereof, or a sequence having at least about 80% identity thereto from said sample; and comparing said expression profile to a reference expression profile, wherein the results of said comparison allows for classification of said specific cancer.

According to certain embodiments, said cancer is selected from the group consisting of liver cancer, brain cancer and gastrointestinal (GI) cancer.

According to one embodiment, said liver cancer is hepatocellular carcimoma (HCC).

According to certain embodiments, said GI cancer is selected from the group consisting of colon, pancreas and stomach cancer.

According to certain embodiments, said brain cancer is selected from the group consisting of glioblastoma, astrocytoma and oligodendroglioma.

The invention further provides a method for identifying liver cancer, the method comprising: obtaining a biological sample from a subject; determining an expression profile of a nucleic acid sequence selected from the group consisting of SEQ ID NOS: 6-13, 32-33, a fragment thereof and a sequence having at least about 80% identity thereto from said sample; and comparing said expression profile to a reference expression profile, wherein the comparison of said expression profile to said reference expression profile allows for the identification of said liver cancer.

The invention further provides a method to distinguish between hepatocellular carcimoma (HCC) and metastasis to the liver, the method comprising: obtaining a biological sample from a subject; determining an expression profile of a nucleic acid sequence selected from the group consisting of SEQ ID NOS: 6-13, 32-33, a fragment thereof and a sequence having at least about 80% identity thereto from said sample; and comparing said expression profile to a reference expression profile, wherein the comparison of said expression profile to said reference expression profile is indicative of hepatocellular carcimoma (HCC) or metastasis to the liver.

According to some embodiments the nucleic acid sequence is selected from the group consisting of SEQ ID NOS: 6, 8, 10, 12, a fragment thereof and a sequence having at least about 80% identity thereto, wherein relatively high expression levels of any of said nucleic acid sequence, as compared to said reference expression profile, is indicative of metastasis to the liver.

According to one embodiment, the liver metastasis is adenocarcinoma.

The invention further provides a method for identifying brain cancer, the method comprising: obtaining a biological sample from a subject; determining an expression profile of a nucleic acid sequence selected from the group consisting of SEQ ID NOS: 14-27, a fragment thereof and a sequence having at least about 80% identity thereto from said sample; and comparing said expression profile to a reference expression profile, wherein the comparison of said expression profile to said reference expression profile allows for the identification of said brain cancer.

The invention further provides a method to distinguish between primary brain tumor and metastasis to the brain, the method comprising: obtaining a biological sample from a subject; determining an expression profile of a nucleic acid sequence selected from the group consisting of SEQ ID NOS: 14-27, a fragment thereof and a sequence having at least about 80% identity thereto from said sample; and comparing said expression profile to a reference expression profile, wherein the comparison of said expression profile to said reference expression profile is indicative of primary brain tumor or metastasis to the brain.

According to some embodiments the nucleic acid sequence is selected from the group consisting of SEQ ID NOS: 14, 20, a fragment thereof and a sequence having at least about 80% identity thereto, wherein relatively high expression levels of any of said nucleic acid sequence, as compared to said reference expression profile, is indicative of primary brain tumor.

The invention further provides a method to distinguish between primary brain tumor and other primary cancers, the method comprising: obtaining a biological sample from a subject; determining an expression profile of a nucleic acid sequence selected from the group consisting of SEQ ID NOS: 14-27, a fragment thereof and a sequence having at least about 80% identity thereto from said sample; and comparing said expression profile to a reference expression profile, wherein the comparison of said expression profile to said reference expression profile is indicative of primary brain tumor or other primary cancers.

The invention further provides a method for identifying a gastrointestinal (GI) cancer, the method comprising: obtaining a biological sample from a subject; determining an expression profile of a nucleic acid sequence selected from the group consisting of SEQ ID NOS: 1-5, a fragment thereof and a sequence having at least about 80% identity thereto from said sample; and comparing said expression profile to a reference expression profile, wherein the comparison of said expression profile to said reference expression profile allows for the identification of said GI cancer.

The invention further provides a method to distinguish between primary GI and non-GI tumor, the method comprising: obtaining a biological sample from a subject; determining an expression profile of a nucleic acid sequence selected from the group consisting of SEQ ID NOS: 1-5, a fragment thereof and a sequence having at least about 80% identity thereto from said sample; and comparing said expression profile to a reference expression profile, wherein the comparison of said expression profile to said reference expression profile is indicative of primary GI or non-GI tumor.

According to some embodiments, said primary GI tumor is selected from the group consisting of colon, pancreas and stomach tumor.

According to other embodiments, said non-GI tumor is selected from the group consisting of lung and breast tumor.

According to some embodiments, said sample is selected from the group consisting of bodily fluid, a cell line and a tissue sample. According to other embodiments, said tissue is a fresh, frozen, fixed, wax-embedded or formalin fixed paraffin-embedded (FFPE) tissue.

The classification method of the present invention further comprises a classifier algorithm, said classifier algorithm is selected from the group consisting of logistic regression classifier, linear regression classifier, nearest neighbor classifier (including K nearest neighbors), neural network classifier, Gaussian mixture model (GMM) classifier and Support Vector Machine (SVM) classifier. The classifier may use a decision tree structure (including binary tree) or a voting (including weighted voting) scheme to compare one or more models which compare one or more classes to other classes.

According to some embodiments the nucleic acid sequence expression profile is determined by a method selected from the group consisting of nucleic acid hybridization and nucleic acid amplification. According to some embodiments the nucleic acid hybridization is performed using a solid-phase nucleic acid biochip array or in situ hybridization.

According to some embodiments the nucleic acid amplification method is real-time PCR. The real-time PCR method may comprise forward and reverse primers. According to some embodiments the forward primer comprises a sequence selected from the group consisting of SEQ ID NOS: 34-38. According to some embodiments the reverse primer comprises SEQ ID NO: 44.

According to additional embodiments the real-time PCR method further comprises a probe. According to some embodiments the probe comprises a sequence selected from the group consisting of a sequence that is complementary to a sequence selected from SEQ ID NOS: 1-33; a fragment thereof and a sequence having at least about 80% identity thereto. According to additional embodiments the probe comprises a sequence selected from the group consisting of SEQ ID NOS: 39-43.

According to another aspect, the present invention provides a kit for cancer classification, said kit comprising a probe comprising a sequence selected from the group consisting of a sequence that is complementary to a sequence selected from SEQ ID NOS: SEQ ID NOS: 1-33; a fragment thereof and a sequence having at least about 80% identity thereto.

According to certain embodiments, said cancer is selected from the group consisting of liver cancer, brain cancer and gastrointestinal (GI) cancer.

According to some embodiments, said cancer is brain cancer. According to certain embodiments, said probe comprises a sequence selected from the group consisting of SEQ ID NOS: 39-43. According to other embodiments, said the kit further comprises a forward primer selected from the group consisting of SEQ ID NOS: 34-38. According to other embodiments, said the kit further comprises a reverse primer comprising SEQ ID NO: 44.

These and other embodiments of the present invention will become apparent in conjunction with the figures, description and claims that follow.

BRIEF DESCRIPTION OF THE DRAWINGS

FIGS. 1A-D demonstrate the identification of non-HCC epithelial tumor samples and metastases using microRNA biomarkers. FIG. 1A. Expression levels (microarray data) of hsa-miR-122a (SEQ ID NO: 32) and hsa-miR-200b (SEQ ID NO: 12) in 30 HCC samples (squares), 63 non-HCC primary tumors of epithelial origin (diamonds), 46 samples of adenocarcinoma metastases to the liver of known origin (circles) and 5 samples of adenocarcinoma metastases to the liver of unknown origin (stars). Expression level of hsa-miR-122a is high in all samples taken from liver, including primary and metastases. Expression level of hsa-miR-200b is high in samples of non-liver origin, both primary and metastases. FIG. 1B. Expression levels (microarray data) of hsa-miR-141 (SEQ ID NO: 6) and hsa-miR-200c (SEQ ID NO: 8) in the same samples. The solid line marks the line where $C_1 \equiv [\log 2(\text{hsa-miR-141}) + \log 2(\text{hsa-miR-200c})] = 18$, the dashed lines mark $C_1 = 20$ (upper line) and $C_1 = 16$ (lower line). All samples with $C_1 < 16$ are HCC, and all samples with $C_1 > 20$ are non-HCC. The sharp threshold at $C_1 = 18$ is accurate in >97% of 144 samples. FIG. 1C. Expression levels (qRT-PCR data, 50 minus normalized $C_t$) of hsa-miR-122a and hsa-miR-200b in 5 HCC samples (squares), 19 non-HCC primary tumors of epithelial origin (diamonds), and 7 samples of adenocarcinoma metastases to the liver of known origin (circles). Expression level of hsa-miR-122a is high in all samples taken from liver, including primary and metastases. FIG. 1D. Expression levels (qRT-PCR) of hsa-miR-141 and hsa-miR-200c in the same samples. The solid line marks the line where $C_{RT} = [(\text{hsa-miR-141}) + (\text{hsa-miR-200c})] = 34$. With the exception of one renal cell carcinoma metastasis to the liver, all samples with $C_{RT} < 34$ are HCC, and all samples with $C_{RT} > 34$ are non-HCC.

FIG. 2A. Expression levels of hsa-miR-194 (SEQ ID NO: 1) and hsa-miR-205 (SEQ ID NO: 4) in 24 primary tumor samples of gastrointestinal (GI) origin (squares) and 39 primary tumors from breast or lung (diamonds). The dashed gray line marks the line where (hsa-miR-205)=(hsa-miR-194)/2 (see methods).

FIG. 3A. Expression levels of hsa-miR-200a (SEQ ID NO: 10) and hsa-miR-200b (SEQ ID NO: 12) in 30 HCC samples (squares) and 63 non-HCC primary tumors of epithelial origin (diamonds). The solid gray line marks the line where Cab≡[log 2(hsa-miR-200a)+log 2(hsa-miR-200b)]=17.7. Only four HCC samples have Cab>17.7, and only three non-HCC lung tumor samples have Cab<17.7.

FIG. 4A. Expression levels of hsa-miR-124a (SEQ ID NO: 16) and hsa-miR-219-5p (SEQ ID NO: 24) in 15 brain primary tumors including GBM (squares), astrocytoma (triangles), oligodendroglioma (upside down triangles); 187 primary tumors from other tissues (diamonds), 50 brain metastases originating from various tissues (circles) and 2 normal brain samples (stars). Expression levels of hsa-miR-124 and hsa-miR-219-5p are higher in brain primary tumors compared to primary tumors from other tissues. The solid line marks the line where $C_0 \equiv [\log 2(\text{hsa-miR-124}) + \log 2(\text{hsa-miR-219-5p})] = 16.8$, and provides perfect separation between brain primary and other primary tumors. The expression levels of hsa-miR-124 and hsa-miR-219-5p in metastatic samples span a wide range on both sides of the separating line.

FIG. 5A. Hsa-miR-128a (SEQ ID NO: 28) and hsa-miR-128b (SEQ ID NO: 30) have highly correlated expression values. These microRNAs are high in brain primary tumors, low in other primary tumors, and intermediate in brain metastasis samples.

FIG. 6A. Expression levels (50-$C_t$) of hsa-miR-124 (SEQ ID NO: 16) and hsa-miR-9 (SEQ ID NO: 27) in 16 brain primary tumors (squares), 15 primary tumors from other tissues (diamonds) and 16 brain metastases originating from various tissues (circles). Expression levels of hsa-miR-124 and hsa-miR-9 are higher in brain primary tumors compared to primary tumors from other tissues. The expression levels of hsa-miR-124 in metastatic samples span a wide range and are more similar to brain primary tumors; the expression levels of hsa-miR-9 in metastatic samples are more similar to the non-brain primary tumors.

DETAILED DESCRIPTION OF THE INVENTION

Figure 1D:
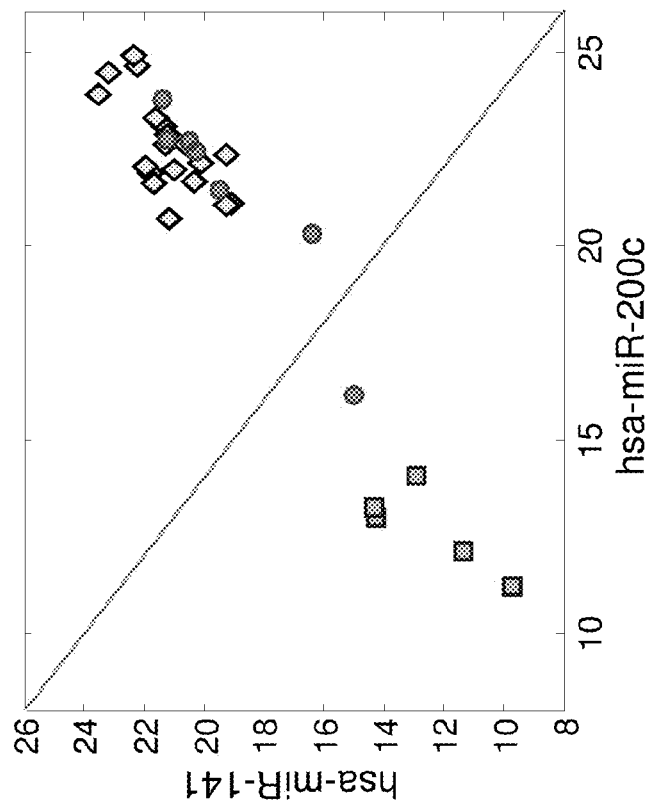

The invention is based on the discovery that specific nucleic acids (SEQ ID NOS: 1-44) may be used for the classification of cancers. The present invention provides a sensitive, specific and accurate method which may be used to distinguish between different tumor origins and between primary and metastatic malignancies.

Metastatic tumors account for the overwhelming majority of all hepatic malignancies in the non cirrhotic liver. In the cirrhotic liver, however, primary hepatic malignancies are more common than metastatic tumors. Carcinomas of the lung, breast, colon and pancreas are the most common primary sites in adults. The distinction between primary and metastatic malignancy in the liver is of both therapeutic and prognostic significance.

In many cases the differential diagnosis of liver tumor includes hepatocellular carcinoma versus metastatic tumor. Some metastases, as from renal origin, can mimic hepatocellular carcinoma, and metastatic tumor may invade liver-cell plates, giving a false impression of primary carcinoma arising within them. Primary extrahepatic carcinomas of the stomach and colon and carcinoma of sex cord-stromal tumors of the ovary may closely resemble HCC in both their morphology and immunoexpression of CEA and alfafeto-protein.

Metastatic tumors tend to recapitulate their appearance in the primary organ and specific tumor types generally maintain consistent cytologic appearance. Adenocarcinoma, although frequently recognizable as an entity, presents the greatest difficulty for those attempting to make a specific diagnosis as to site of origin.

According to the present invention, the ability of microRNA biomarkers to differentiate HCC from metastatic liver tumors of various origins was demonstrated. The expression of human microRNAs in 144 hepatic and non-hepatic tumors was examined by microRNA microarray. The expression of hsa-miR-141 (SEQ ID NO: 6) and hsa-miR-200c (SEQ ID NO: 8) was significantly higher in non-hepatic primary tumors compared to HCC (p-value<$10^{-9}$ for each) and allows highly accurate differential diagnosis of hepatocellular carcinoma from metastatic adenocarcinoma (sensitivity=98%; specificity=93%) Similar results were obtained by using the combination of hsa-miR-200a (SEQ ID NO: 10) and hsa-miR-200b (SEQ ID NO: 12).

hsa-miR-141, hsa-miR-200a, hsa-miR-200b and hsa-miR-200c are part of one predicted polycistronic pri-microRNA, in an intronic region of a transcription unit (EST with no ORF) on Chr.12p13.31 (Landgraf, P., et al., Cell, 2007. 129(7): p. 1401-14). Hsa-miR-194 (SEQ ID NO: 1) and hsa-miR-205 (SEQ ID NO: 4) were differentially expressed in primary GI and non-GI tumors (e.g., lung or breast adenocarcinomas) (p-value<0.01 for hsa-miR-205 and p-value<$10^{-11}$ for hsa-miR-194), and may serve as potent biomarkers for the identification of tumors of GI origin.

The combination of another pair of microRNAs, hsa-miR-92b (SEQ ID NO: 14) and hsa-miR-9* (SEQ ID NO: 20), was capable of identifying primary brain tumors (p-value<2.5e-4 for each compared to normal brain, p-value<5e-25 for each compared to other primary and metastatic tumors). The combination of another pair of microRNAs, hsa-miR-124a (SEQ ID NO: 16) and hsa-miR-219 (SEQ ID NO: 24), was capable of differentiating normal brain and primary brain tumors from other primary tumors (p-value<2e-44 for each) or from brain metastases (p-value<6e-6 for each).

The present invention provides diagnostic assays and methods, both quantitative and qualitative for detecting, diagnosing, monitoring, staging and prognosticating cancers by comparing levels of the specific microRNA molecules of the invention. Such levels are preferably measured in at least one of biopsies, tumor samples, cells, tissues and/or bodily fluids, including determination of normal and abnormal levels. The present invention provides methods for diagnosing the presence of a specific cancer by analyzing for changes in levels of said microRNA molecules in biopsies, tumor samples, cells, tissues or bodily fluids.

In the present invention, determining the presence of said microRNA levels in biopsies, tumor samples, cells, tissues or bodily fluid, is particularly useful for discriminating between different cancers.

All the methods of the present invention may optionally include measuring levels of other cancer markers. Other cancer markers, in addition to said microRNA molecules, useful in the present invention will depend on the cancer being tested and are known to those of skill in the art.

Assay techniques that can be used to determine levels of gene expression, such as the nucleic acid sequence of the present invention, in a sample derived from a patient are well known to those of skill in the art. Such assay methods include, without limitation, radioimmunoassays, reverse transcriptase PCR (RT-PCR) assays, immunohistochemistry assays, in situ hybridization assays, competitive-binding assays, Northern Blot analyses, ELISA assays and biochip analysis.

In some embodiments of the invention, correlations and/or hierarchical clustering can be used to assess the similarity of the expression level of the nucleic acid sequences of the invention between a specific sample and different exemplars of cancer samples, by setting an arbitrary threshold for assigning a sample or cancer sample to one of two groups. Alternatively, in a preferred embodiment, the threshold for assignment is treated as a parameter, which can be used to quantify the confidence with which samples are assigned to each class. The threshold for assignment can be scaled to favor sensitivity or specificity, depending on the clinical scenario. The correlation value to the reference data generates a continuous score that can be scaled.

Definitions

Before the present compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Aberrant Proliferation

As used herein, the term "aberrant proliferation" means cell proliferation that deviates from the normal, proper, or expected course. For example, aberrant cell proliferation may include inappropriate proliferation of cells whose DNA or other cellular components have become damaged or defective. Aberrant cell proliferation may include cell proliferation whose characteristics are associated with an indication caused by, mediated by, or resulting in inappropriately high levels of cell division, inappropriately low levels of apoptosis, or both. Such indications may be characterized, for example, by single or multiple local abnormal proliferations of cells, groups of cells, or tissue(s), whether cancerous or non-cancerous, benign or malignant.

About

As used herein, the term "about" refers to +/−10%.

Attached

"Attached" or "immobilized" as used herein to refer to a probe and a solid support may mean that the binding between the probe and the solid support is sufficient to be stable under conditions of binding, washing, analysis, and removal. The binding may be covalent or non-covalent. Covalent bonds may be formed directly between the probe and the solid support or may be formed by a cross linker or by inclusion of a specific reactive group on either the solid support or the probe or both molecules. Non-covalent binding may be one or more of electrostatic, hydrophilic, and hydrophobic interactions. Included in non-covalent binding is the covalent attachment of a molecule, such as streptavidin, to the support and the non-covalent binding of a biotinylated probe to the streptavidin. Immobilization may also involve a combination of covalent and non-covalent interactions.

Biological Sample

"Biological sample" as used herein may mean a sample of biological tissue or fluid that comprises nucleic acids. Such samples include, but are not limited to, tissue or fluid isolated from subjects. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from animal or patient tissues. Biological samples may also be blood, a blood fraction, urine, effusions, ascitic fluid, amniotic fluid, saliva, cerebrospinal fluid, cervical secretions, vaginal secretions, endometrial secretions, gastrointestinal secretions, bronchial secretions, sputum, cell line, tissue sample, or secretions from the breast. A biological sample may be provided by removing a sample of cells from a subject but can also be accomplished by using previously isolated cells (e.g., isolated by another person, at another time, and/or for another purpose), or by performing the methods described herein in vivo. Archival tissues, such as those having treatment or outcome history, may also be used.

Cancer

The term "cancer" is meant to include all types of cancerous growths or oncogenic processes, metastatic tissues or malignantly transformed cells, tissues, or organs, irrespective of histopathologic type or stage of invasiveness. Examples of cancers include but are nor limited to solid tumors and leukemias, including: apudoma, choristoma, branchioma, malignant carcinoid syndrome, carcinoid heart disease, carcinoma (e.g., Walker, basal cell, basosquamous, Brown-Pearce, ductal, Ehrlich tumor, non-small cell lung, oat cell, papillary, bronchiolar, bronchogenic, squamous cell, and transitional cell), histiocytic disorders, leukemia (e.g., B cell, mixed cell, null cell, T cell, T-cell chronic, HTLV-II-associated, lymphocytic acute, lymphocytic chronic, mast cell, and myeloid), histiocytosis malignant, Hodgkin disease, immunoproliferative small, non-Hodgkin lymphoma, plasmacytoma, reticuloendotheliosis, melanoma, chondroblastoma, chondroma, chondrosarcoma, fibroma, fibrosarcoma, giant cell tumors, histiocytoma, lipoma, liposarcoma, mesothelioma, myxoma, myxosarcoma, osteoma, osteosarcoma, Ewing sarcoma, synovioma, adenofibroma, adenolymphoma, carcinosarcoma, chordoma, craniopharyngioma, dysgerminoma, hamartoma, mesenchymoma, mesonephroma, myosarcoma, ameloblastoma, cementoma, odontoma, teratoma, thymoma, trophoblastic tumor, adeno-carcinoma, adenoma, cholangioma, cholesteatoma, cylindroma, cystadenocarcinoma, cystadenoma, granulosa cell tumor, gynandroblastoma, hepatoma, hidradenoma, islet cell tumor, Leydig cell tumor, papilloma, Sertoli cell tumor, theca cell tumor, leiomyoma, leiomyosarcoma, myoblastoma, myosarcoma, rhabdomyoma, rhabdomyosarcoma, ependymoma, ganglioneuroma, glioma, medulloblastoma, meningioma, neurilemmoma, neuroblastoma, neuroepithelioma, neurofibroma, neuroma, paraganglioma, paraganglioma nonchromaffin, angiokeratoma, angiolymphoid hyperplasia with eosinophilia, angioma sclerosing, angiomatosis, glomangioma, hemangioendothelioma, hemangioma, hemangiopericytoma, hemangiosarcoma, lymphangioma, lymphangiomyoma, lymphangiosarcoma, pinealoma, carcinosarcoma, chondrosarcoma, cystosarcoma, phyllodes, fibrosarcoma, hemangiosarcoma, leimyosarcoma, leukosarcoma, liposarcoma, lymphangiosarcoma, myosarcoma, myxosarcoma, ovarian carcinoma, rhabdomyosarcoma, sarcoma (e.g., Ewing, experimental, Kaposi, and mast cell), neurofibromatosis, and cervical dysplasia, and other conditions in which cells have become immortalized or transformed.

Classification

The term classification refers to a procedure and/or algorithm in which individual items are placed into groups or classes based on quantitative information on one or more characteristics inherent in the items (referred to as traits, variables, characters, features, etc) and based on a statistical model and/or a training set of previously labeled items. A "classification tree" is a decision tree that places categorical variables into classes.

Ct

Ct signals represent the first cycle of PCR where amplification crosses a threshold (cycle threshold) of fluorescence. Accordingly, low values of Ct represent high abundance or expression levels of the microRNA.

In some embodiments the PCR Ct signal is normalized such that the normalized Ct remains inversed from the expression level. In other embodiments the PCR Ct signal may be normalized and then inverted such that low normalized-inverted Ct represents low abundance or expression levels of the microRNA.

Complement

"Complement" or "complementary" as used herein to refer to a nucleic acid may mean Watson-Crick (e.g., A-T/U and C-G) or Hoogsteen base pairing between nucleotides or nucleotide analogs of nucleic acid molecules. A full complement or fully complementary may mean 100% complementary base pairing between nucleotides or nucleotide analogs of nucleic acid molecules.

Data Processing Routine

As used herein, a "data processing routine" refers to a process that can be embodied in software that determines the biological significance of acquired data (i.e., the ultimate results of an assay or analysis). For example, the data processing routine can make determination of tissue of origin based upon the data collected. In the systems and methods herein, the data processing routine can also control the data collection routine based upon the results determined. The data processing routine and the data collection routines can be integrated and provide feedback to operate the data acquisition, and hence provide assay-based judging methods.

Data Set

As use herein, the term "data set" refers to numerical values obtained from the analysis, These numerical values associated with analysis may be values such as peak height and area under the curve.

Data Structure

As used herein the term "data structure" refers to a combination of two or more data sets, applying one or more mathematical manipulations to one or more data sets to obtain one or more new data sets, or manipulating two or more data sets into a form that provides a visual illustration of the data in a new way. An example of a data structure prepared from manipulation of two or more data sets would be a hierarchical cluster.

Detection

"Detection" means detecting the presence of a component in a sample. Detection also means detecting the absence of a component. Detection also means measuring the level of a component, either quantitatively or qualitatively.

Differential Expression

"Differential expression" means qualitative or quantitative differences in the temporal and/or cellular gene expression patterns within and among cells and tissue. Thus, a differentially expressed gene may qualitatively have its expression altered, including an activation or inactivation, in, e.g., normal versus disease tissue. Genes may be turned on or turned off in a particular state, relative to another state thus permitting comparison of two or more states. A qualitatively regulated gene may exhibit an expression pattern within a state or cell type which may be detectable by standard techniques. Some genes may be expressed in one state or cell type, but not in both. Alternatively, the difference in expression may be quantitative, e.g., in that expression is modulated, either up-regulated, resulting in an increased amount of transcript, or down-regulated, resulting in a decreased amount of transcript. The degree to which expression differs need only be large enough to quantify via standard characterization techniques such as expression arrays, quantitative reverse transcriptase PCR, northern analysis, real-time PCR, in situ hybridization and RNase protection.

Expression Profile

The term "expression profile" is used broadly to include a genomic expression profile, e.g., an expression profile of microRNAs. Profiles may be generated by any convenient means for determining a level of a nucleic acid sequence e.g. quantitative hybridization of microRNA, labeled microRNA, amplified microRNA, cRNA, etc., quantitative PCR, ELISA for quantitation, and the like, and allow the analysis of differential gene expression between two samples. A subject or patient tumor sample, e.g., cells or collections thereof, e.g., tissues, is assayed. Samples are collected by any convenient method, as known in the art. Nucleic acid sequences of interest are nucleic acid sequences that are found to be predictive, including the nucleic acid sequences provided above, where the expression profile may include expression data for 5, 10, 20, 25, 50, 100 or more of, including all of the listed nucleic acid sequences. According to some embodiments, the term "expression profile" means measuring the abundance of the nucleic acid sequences in the measured samples.

Expression Ratio

"Expression ratio" as used herein refers to relative expression levels of two or more nucleic acids as determined by detecting the relative expression levels of the corresponding nucleic acids in a biological sample.

FDR

When performing multiple statistical tests, for example in comparing the signal between two groups in multiple data features, there is an increasingly high probability of obtaining false positive results, by random differences between the groups that can reach levels that would otherwise be considered as statistically significant. In order to limit the proportion of such false discoveries, statistical significance is defined only for data features in which the differences reached a p-value (by two-sided t-test) below a threshold, which is dependent on the number of tests performed and the distribution of p-values obtained in these tests.

Fragment

"Fragment" is used herein to indicate a non-full length part of a nucleic acid. Thus, a fragment is itself also a nucleic acid.

Gene

"Gene" used herein may be a natural (e.g., genomic) or synthetic gene comprising transcriptional and/or translational regulatory sequences and/or a coding region and/or non-translated sequences (e.g., introns, 5'- and 3'-untranslated sequences). The coding region of a gene may be a nucleotide sequence coding for an amino acid sequence or a functional RNA, such as tRNA, rRNA, catalytic RNA, siRNA, miRNA or antisense RNA. A gene may also be an mRNA or cDNA corresponding to the coding regions (e.g., exons and miRNA) optionally comprising 5'- or 3'-untranslated sequences linked thereto. A gene may also be an amplified nucleic acid molecule produced in vitro comprising all or a part of the coding region and/or 5'- or 3'-untranslated sequences linked thereto.

Groove Binder/Minor Groove Binder (MGB)

"Groove binder" and/or "minor groove binder" may be used interchangeably and refer to small molecules that fit into the minor groove of double-stranded DNA, typically in a sequence-specific manner. Minor groove binders may be long, flat molecules that can adopt a crescent-like shape and thus, fit snugly into the minor groove of a double helix, often displacing water. Minor groove binding molecules may typically comprise several aromatic rings connected by bonds with torsional freedom such as furan, benzene, or pyrrole rings. Minor groove binders may be antibiotics such as netropsin, distamycin, berenil, pentamidine and other aromatic diamidines, Hoechst 33258, SN 6999, aureolic anti-tumor drugs such as chromomycin and mithramycin, CC-1065, dihydrocyclopyrroloindole tripeptide ($DPI_3$), 1,2-dihydro-(3H)-pyrrolo[3,2-e]indole-7-carboxylate ($CDPI_3$), and related compounds and analogues, including those described in Nucleic Acids in Chemistry and Biology, 2d ed., Blackburn and Gait, eds., Oxford University Press, 1996, and PCT Published Application No. WO 03/078450, the contents of which are incorporated herein by reference. A minor groove binder may be a component of a primer, a probe, a hybridization tag complement, or combinations thereof. Minor groove binders may increase the $T_m$ of the primer or a probe to which they are attached, allowing such primers or probes to effectively hybridize at higher temperatures.

Host Cell

"Host cell" used herein may be a naturally occurring cell or a transformed cell that may contain a vector and may support replication of the vector. Host cells may be cultured cells, explants, cells in vivo, and the like. Host cells may be prokaryotic cells such as E. coli, or eukaryotic cells such as yeast, insect, amphibian, or mammalian cells, such as CHO and HeLa.

Identity

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

In Situ Detection

"In situ detection" as used herein means the detection of expression or expression levels in the original site hereby meaning in a tissue sample such as biopsy.

k-Nearest Neighbor

The phrase "k-nearest neighbor" refers to a classification method that classifies a point by calculating the distances between the point and points in the training data set. Then it assigns the point to the class that is most common among its k-nearest neighbors (where k is an integer).

Label

"Label" as used herein may mean a composition detectable by spectroscopic, photochemical, biochemical, immunochemical, chemical, or other physical means. For example, useful labels include $^{32}P$, fluorescent dyes, electron-dense reagents, enzymes (e.g., as commonly used in an ELISA), biotin, digoxigenin, or haptens and other entities which can be made detectable. A label may be incorporated into nucleic acids and proteins at any position.

Liver Cancer

"Liver cancer" means malignancy of the liver, either a primary cancer or metastasized cancer. In certain embodiments, liver cancer includes, but is not limited to, cancer arising from hepatocytes, such as, for example, hepatomas and hepatocellular carcinomas; fibrolamellar; and cholangiocarcinomas (or bile duct cancer).

Logistic Regression

Logistic regression is part of a category of statistical models called generalized linear models. Logistic regression can allows one to predict a discrete outcome, such as group membership, from a set of variables that may be continuous, discrete, dichotomous, or a mix of any of these. The dependent or response variable can be dichotomous, for example, one of two possible types of cancer. Logistic regression models the natural log of the odds ratio, i.e. the ratio of the probability of belonging to the first group (P) over the probability of belonging to the second group (1−P), as a linear combination of the different expression levels (in log-space). The logistic regression output can be used as a classifier by prescribing that a case or sample will be classified into the first type is P is greater than 0.5 or 50%. Alternatively, the calculated probability P can be used as a variable in other contexts such as a 1D or 2D threshold classifier.

1D/2D Threshold Classifier

"1D/2D threshold classifier" used herein may mean an algorithm for classifying a case or sample such as a cancer sample into one of two possible types such as two types of cancer. For a 1D threshold classifier, the decision is based on one variable and one predetermined threshold value; the sample is assigned to one class if the variable exceeds the threshold and to the other class if the variable is less than the threshold. A 2D threshold classifier is an algorithm for classifying into one of two types based on the values of two variables. A threshold may be calculated as a function (usually a continuous or even a monotonic function) of the first variable; the decision is then reached by comparing the second variable to the calculated threshold, similar to the 1D threshold classifier.

Metastasis

"Metastasis" means the process by which cancer spreads from the place at which it first arose as a primary tumor to other locations in the body. The metastatic progression of a primary tumor reflects multiple stages, including dissociation from neighboring primary tumor cells, survival in the circulation, and growth in a secondary location.

Nucleic Acid

"Nucleic acid" or "oligonucleotide" or "polynucleotide" used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modified nucleotides also include nucleotides conjugated with cholesterol through, e.g., a hydroxyprolinol linkage as described in Krutzfeldt et al., Nature 438:685-689 (2005), Soutschek et al., Nature 432:173-178 (2004), and U.S. Patent Publication No. 20050107325, which are incorporated herein by reference. Additional modified nucleotides and nucleic acids are described in U.S. Patent Publication No. 20050182005, which is incorporated herein by reference. Modifications of the ribose-phosphate backbone may be done for a variety of reasons, e.g., to increase the stability and half-life of such molecules in physiological environments, to enhance diffusion across cell membranes, or as probes on a biochip. The backbone modification may also enhance resistance to degradation, such as in the harsh endocytic environment of cells. The backbone modification may also reduce nucleic acid clearance by hepatocytes, such as in the liver and kidney. Mixtures of naturally occurring nucleic acids and analogs may be made; alternatively, mixtures of different nucleic acid analogs, and mixtures of naturally occurring nucleic acids and analogs may be made.

Probe

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

Reference Expression Profile

As used herein, the phrase "reference expression profile" refers to a criterion expression value to which measured values are compared in order to determine the detection of a subject with lung cancer. The reference expression profile may be based on the abundance of the nucleic acids, or may be based on a combined metric score thereof.

Sensitivity

"sensitivity" used herein may mean a statistical measure of how well a binary classification test correctly identifies a condition, for example how frequently it correctly classifies a cancer into the correct type out of two possible types. The sensitivity for class A is the proportion of cases that are determined to belong to class "A" by the test out of the cases that are in class "A", as determined by some absolute or gold standard.

Specificity

"specificity" used herein may mean a statistical measure of how well a binary classification test correctly identifies a condition, for example how frequently it correctly classifies a cancer into the correct type out of two possible types. The sensitivity for class A is the proportion of cases that are determined to belong to class "not A" by the test out of the cases that are in class "not A", as determined by some absolute or gold standard.

Stringent Hybridization Conditions

"Stringent hybridization conditions" used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

Substantially Complementary

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

Substantially Identical

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

Subject

As used herein, the term "subject" refers to a mammal, including both human and other mammals. The methods of the present invention are preferably applied to human subjects.

Target

"Target" as used herein may mean a polynucleotide that may be bound by one or more probes under stringent hybridization conditions.

Threshold Expression Profile

As used herein, the phrase "threshold expression profile" refers to a criterion expression profile to which measured values are compared in order to classify a cancer.

Tissue Sample

As used herein, a tissue sample is tissue obtained from a tissue biopsy using methods well known to those of ordinary skill in the related medical arts. The phrase "suspected of being cancerous" as used herein means a cancer tissue sample believed by one of ordinary skill in the medical arts to contain cancerous cells. Methods for obtaining the sample from the biopsy include gross apportioning of a mass, microdissection, laser-based microdissection, or other art-known cell-separation methods.

Tumor

"Tumor" as used herein, refers to all neoplastic cell growth and proliferation, whether malignant or benign, and all pre-cancerous and cancerous cells and tissues.

Variant

"Variant" used herein to refer to a nucleic acid may mean (i) a portion of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequence substantially identical thereto.

Wild Type

As used herein, the term "wild type" sequence refers to a coding, non-coding or interface sequence is an allelic form of sequence that performs the natural or normal function for that sequence. Wild type sequences include multiple allelic forms of a cognate sequence, for example, multiple alleles of a wild type sequence may encode silent or conservative changes to the protein sequence that a coding sequence encodes.

The present invention employs miRNAs and related nucleic acids for the identification, classification and diagnosis of specific cancers.

microRNA Processing

A gene coding for a miRNA may be transcribed leading to production of a miRNA primary transcript known as the pri-miRNA. The pri-miRNA may comprise a hairpin with a stem and loop. The stem of the hairpin may comprise mismatched bases. The pri-miRNA may comprise several hairpins in a polycistronic structure.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (~10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. MiRNA* sequences may be found in libraries of cloned miRNAs but typically at lower frequency than the miRNAs.

Although initially present as a double-stranded species with miRNA*, the miRNA may eventually become incorporated as a single-stranded RNA into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The RISC may identify target nucleic acids based on high levels of complementarity between the miRNA and the mRNA, especially by nucleotides 2-7 of the miRNA. Only one case has been reported in animals where the interaction between the miRNA and its target was along the entire length of the miRNA. This was shown for mir-196 and Hox B8 and it was further shown that mir-196 mediates the cleavage of the Hox B8 mRNA (Yekta et al 2004, Science 304-594). Otherwise, such interactions are known only in plants (Bartel & Bartel 2003, Plant Physiol 132-709).

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 GenesDev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut may be between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

Nucleic Acid

Nucleic acids are provided herein. The nucleic acid may comprise the sequence of SEQ ID NOS: 1-44 or variants thereof. The variant may be a complement of the referenced nucleotide sequence. The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto.

The nucleic acid may have a length of from 10 to 250 nucleotides. The nucleic acid may have a length of at least 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 125, 150, 175, 200 or 250 nucleotides. The nucleic acid may be synthesized or expressed in a cell (in vitro or in vivo) using a synthetic gene described herein. The nucleic acid may be synthesized as a single strand molecule and hybridized to a substantially complementary nucleic acid to form a duplex. The nucleic acid may be introduced to a cell, tissue or organ in a single- or double-stranded form or capable of being expressed by a synthetic gene using methods well known to those skilled in the art, including as described in U.S. Pat. No. 6,506,559 which is incorporated by reference.

Nucleic Acid Complexes

The nucleic acid may further comprise one or more of the following: a peptide, a protein, a RNA-DNA hybrid, an antibody, an antibody fragment, a Fab fragment, and an aptamer.

Pri-miRNA

The nucleic acid may comprise a sequence of a pri-miRNA or a variant thereof. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. The sequence of the pri-miRNA may comprise the sequence of SEQ ID NOS: 1-33 or variants thereof.

The pri-miRNA may comprise a hairpin structure. The hairpin may comprise first and second nucleic acid sequences that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides. The pri-miRNA may comprise at least 19% adenosine nucleotides, at least 16% cytosine nucleotides, at least 23% thymine nucleotides and at least 19% guanine nucleotides.

Pre-miRNA

The nucleic acid may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of SEQ ID NOS: 1-33 or variants thereof.

miRNA

The nucleic acid may also comprise a sequence of a miRNA (including miRNA*) or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise the sequence of SEQ ID NOS: 1-33 or variants thereof.

Probes

A probe is also provided comprising a nucleic acid described herein. Probes may be used for screening and diagnostic methods, as outlined below. The probe may be attached or immobilized to a solid substrate, such as a biochip.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides. The probe may comprise a nucleic acid that is complementary to a sequence selected from the group consisting of SEQ ID NOS: 1-27, 32-33; a fragment thereof, and a sequence having at least about 80% identity thereto.

Biochip

A biochip is also provided. The biochip may comprise a solid substrate comprising an attached probe or plurality of probes described herein. The probes may be capable of hybridizing to a target sequence under stringent hybridization conditions. The probes may be attached at spatially defined addresses on the substrate. More than one probe per target sequence may be used, with either overlapping probes or probes to different sections of a particular target sequence. The probes may be capable of hybridizing to target sequences associated with a single disorder appreciated by those in the art. The probes may either be synthesized first, with subsequent attachment to the biochip, or may be directly synthesized on the biochip.

The solid substrate may be a material that may be modified to contain discrete individual sites appropriate for the attachment or association of the probes and is amenable to at least one detection method. Representative examples of substrates include glass and modified or functionalized glass, plastics (including acrylics, polystyrene and copolymers of styrene and other materials, polypropylene, polyethylene, polybutylene, polyurethanes, TeflonJ, etc.), polysaccharides, nylon or nitrocellulose, resins, silica or silica-based materials including silicon and modified silicon, carbon, metals, inorganic glasses and plastics. The substrates may allow optical detection without appreciably fluorescing.

The substrate may be planar, although other configurations of substrates may be used as well. For example, probes may be placed on the inside surface of a tube, for flow-through sample analysis to minimize sample volume. Similarly, the substrate may be flexible, such as flexible foam, including closed cell foams made of particular plastics.

The biochip and the probe may be derivatized with chemical functional groups for subsequent attachment of the two. For example, the biochip may be derivatized with a chemical functional group including, but not limited to, amino groups, carboxyl groups, oxo groups or thiol groups. Using these functional groups, the probes may be attached using functional groups on the probes either directly or indirectly using a linker. The probes may be attached to the solid support by either the 5' terminus, 3' terminus, or via an internal nucleotide.

The probe may also be attached to the solid support non-covalently. For example, biotinylated oligonucleotides can be made, which may bind to surfaces covalently coated with streptavidin, resulting in attachment. Alternatively, probes may be synthesized on the surface using techniques such as photopolymerization and photolithography.

Diagnostic

As used herein the term "diagnosing" refers to classifying a pathology or a symptom, determining a severity of the pathology (grade or stage), monitoring pathology progression, forecasting an outcome of a pathology and/or prospects of recovery.

As used herein the phrase "subject in need thereof" refers to an animal or human subject who is known to have cancer, at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up. According to some embodiments, the subject has a primary tumor. According to other embodiments, the subject has metastatic cancer. According to another embodiment, the subject has cancer of unknown primary (CUP).

Analyzing presence of malignant or pre-malignant cells can be effected in-vivo or ex-vivo, whereby a biological sample (e.g., biopsy) is retrieved. Such biopsy samples comprise cells and may be an incisional or excisional biopsy. Alternatively the cells may be retrieved from a complete resection.

While employing the present teachings, additional information may be gleaned pertaining to the determination of treatment regimen, treatment course and/or to the measurement of the severity of the disease.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

A method of diagnosis is also provided. The method comprises detecting an expression level of a specific cancer-associated nucleic acid in a biological sample. The sample may be derived from a patient. Diagnosis of a specific cancer state in a patient may allow for prognosis and selection of therapeutic strategy. Further, the developmental stage of cells may be classified by determining temporarily expressed specific cancer-associated nucleic acids.

In situ hybridization of labeled probes to tissue arrays may be performed. When comparing the fingerprints between individual samples the skilled artisan can make a diagnosis, a prognosis, or a prediction based on the findings. It is further understood that the nucleic acid sequence which indicate the diagnosis may differ from those which indicate the prognosis and molecular profiling of the condition of the cells may lead to distinctions between responsive or refractory conditions or may be predictive of outcomes.

Kits

A kit is also provided and may comprise a nucleic acid described herein together with any or all of the following: assay reagents, buffers, probes and/or primers, and sterile saline or another pharmaceutically acceptable emulsion and suspension base. In addition, the kits may include instructional materials containing directions (e.g., protocols) for the practice of the methods described herein. The kit may further comprise a software package for data analysis of expression profiles.

For example, the kit may be a kit for the amplification, detection, identification or quantification of a target nucleic acid sequence. The kit may comprise a poly(T) primer, a forward primer, a reverse primer, and a probe.

Detectable Malignancies

Brain Cancer:

Each year, approximately 15,000 cases of high grade astrocytomas (glioblastoma multiforme) are diagnosed in the United States. The number is growing in both pediatric and adult populations. Standard treatments include cytoreductive surgery followed by radiation therapy or chemotherapy. There is no cure, and virtually all patients ultimately succumb to recurrent or progressive disease. The overall survival for grade IV astrocytomas (glioblastoma multiforme) is poor, with 50% of patients dying in the first year after diagnosis.

According to the present invention, brain tumors were directly compared to a wide range of epithelial tumors and metastases to the brain. Using microarray data, it was found that elevated expression of just two microRNAs, hsa-miR-92b (SEQ ID NO: 14) and hsa-miR-9* (SEQ ID NO: 20), is sufficient to distinguish brain primary tumors from tumors derived from non-brain tissues, and most significantly for diagnostic purposes, from metastases located in the brain. This assay was translated to a qRT-PCR platform, using additional samples as a training set to develop a classifier. Validating on an independent set of test samples, it was found that the simple combination of hsa-miR-92b and hsa-miR-9 (SEQ ID NO: 27) (or hsa-miR-9*) can identify brain metastases from brain primary tumors with sensitivity of 88% and specificity of 100%. Thus, economical and relatively easy evaluation of hsa-miR-92b and hsa-miR-9/9* expression, which can be performed robustly using either fresh frozen or fixed materials in the clinical setting, reveals whether neoplastic tissue excised from the brain is brain-derived or represents a metastasis from another tissue. Taken together, the expression data concerning hsa-miR-92b and hsa-miR-9/9* suggest a connection between deregulation of microRNAs, pluripotency, and tumorigenesis.

Liver Cancer:

Primary liver cancer is the fifth most common cancer worldwide. Hepatocellular carcinoma (HCC) accounts for 80% of all liver cancer and the rates of HCC have increased by over 70% in the last two decades in the U.S. The fatality ratio (mortality/incidence) of liver cancer is approximately 1, indicating that the majority of patients live less than a year. Late diagnosis due to lack of clinical symptoms is one of the main reasons for the high fatality ratio. Liver cancer can result from both viral infection and chemical exposure. Known risk factors include hepatitis B and C virus infection. It is not known whether distinct routes to liver cancer affect the same or different cellular pathways. No mutational model has yet been developed for liver cancer as it has been for other cancers. The molecular events that precede neoplastic transformation of the liver are not well understood. With no clearly identified cause, successful treatment options are lacking. Nearly any primary tumor site can deposit metastases in the liver, since the liver filters blood from throughout the body. Most discussions related to the treatment of metastatic tumors in the liver focus on those originating from the colon. In fact, the most common cause of death from colorectal cancer is liver metastasis.

Up to 50% of liver metastases are of colorectal cancer origin, while the remainder metastasizes from a wide variety of primary cancer sites including sarcomas, breast and kidney, as well as neuroendocrine tumors.

HCC may be solitary or multicentric, and it may mimic liver metastases. Furthermore hemangiomas and liver metastases are often confused in imaging methods. In general, the imaging appearances of liver metastases are non-specific, and biopsy specimens are required for histological diagnosis. Various biochemical markers have been proposed to indicate liver metastases. However, the diagnostic accuracy of tumor markers has not yet been defined.

The following examples are presented in order to more fully illustrate some embodiments of the invention. They should, in no way be construed, however, as limiting the broad scope of the invention.

EXAMPLES

Material and Methods

1. Tumor Samples 27 fresh frozen and 141 formalin-fixed paraffin embedded (FFPE) tumor samples obtained from several sources (Sheba Medical Center, Tel-Hashomer, Israel; ABS Inc., Wilmington, Del.; Seoul National University College of Medicine, Seoul, South Korea; Indivumed GmbH, Hamburg, Germany; Soroka University Medical Center, Beer-Sheva, Israel) were used for comparing liver tumors to non-liver tumors and liver metastases. 2 fresh frozen brain normal samples (obtained from Ambion Inc.), 3 fresh-frozen liver tumor samples (obtained from Seoul National University College of Medicine, Seoul, South Korea) and 285 FFPE tumor samples (obtained from Sheba Medical Center, Tel-Hashomer, Israel; Soroka University Medical Center, Beer-Sheva, Israel; Beilinson Hospital, Rabin Medical Center, Petah-Tikva, Israel; ABS Inc., Wilmington, Del.; Tel Aviv Sourasky Medical Center, Tel Aviv, Israel; Bnai Zion Medical Center, Haifa, Israel) were used for comparing brain tumors to normal brain, non-brain tumors and brain metastases. The study protocol was approved by the Research Ethics Board of each of the contributing institutes. Each of the FFPE samples was evaluated by a pathologist for histological type, grade and tumor percentages based on hematoxilin-eosin (H&E) stained slides, performed on the first and/or last sections of the sample. The tumor content was ≥50% in 85% of the FFPE samples. For frozen samples, information was extracted from medical records.

252 of the samples were profiled by microRNA microarray. 14 of these samples and 59 additional samples were profiled by qRT-PCR. Histological classification of the study samples is summarized in Table 1a-b.

TABLE 1a

Summary of sample types, numbers and histology used for comparing liver tumors to non-liver tumors and liver metastases.

| N | Sample category | Detail |
|---|---|---|
| 30 | Liver Primary Tumor | 30 Liver (7 FFPE, 23 fresh) |
| 63 | Non-Liver Primary Tumor | 15 Breast (FFPE, 1 identified as adenocarcinoma) 14 Colon (FFPE, 10 identified as adenocarcinoma) 24 Lung (FFPE, 7 adenocarcinoma, 8 squamous cell carcinoma, 1 large cell carcinoma, 3 NSCLC, 1 neuroendocrine SCLC, 1 mixed adeno-squamous carcinoma) 5 Pancreas (FFPE, 4 exocrine adenocarcinoma and 1 pancreatic ducr adenocarcinoma) 5 Stomach (FFPE, adenomcarcinoma) |
| 46 | Liver Metastasis of Known Origin | 3 Breast (FFPE, adenocarcinoma) 36 Colon (35 FFPE and 1 fresh, adenocarcinoma) 1 Lung (FFPE, adenocarcinoma) 2 Pancreas (FFPE, adenocarcinoma) 3 Rectum (fresh, adenomcarcinoma) 1 Stomach (FFPE, adenomcarcinoma) |
| 5 | Liver Metastasis of Unknown Origin | 5 Unknown (FFPE, adenocarcinoma) |

| N | Additional samples in qRT-PCR validation set, by category | Detail |
|---|---|---|
| 5 | Liver Primary Tumor | 5 Liver (FFPE) |
| 18 | Non-Liver Primary Tumor Liver Metastasis of Known | 2 Ovary and 16 Lung (FFPE) |
| 1 | Origin | 1 Kidney (FFPE) |

TABLE 1b

Summary of sample types, numbers and histology used for comparing brain tumors to normal brain, non-brain tumors and brain metastases

| N | Samples in microarray data - by category | Detail |
|---|---|---|
| 15 | Brain primary tumors | anaplastic astrocytoma (2), anaplastic oligodendroglioma (1), glioblastoma multiforme (7), low grade astrocytoma (3), oligodendroglioma (2) |
| 187 | Other primary tumors | adipose liposarcoma (4), bladder (1 transitional cell carcinoma), breast (3 including 1 infiltrating lobular carcinoma), cervix (3 adenocarcinoma, 2 squamous cell carcinoma), colon (4 adenocarcinoma), endometrium (7 adenocarcinoma), esophagus (2 adenocarcinoma, 5 squamous cell carcinoma), esophagus-stomach (7 adenocarcinoma), gallbladder (3 adenocarcinoma), kidney (6 renal cell carcinoma), larynx (4 squamous cell carcinoma), liver (2 hepatocellular carcinoma), lung (7 neuroendocrine carcinoid, 1 neuroendocrine large cell, 1 neuroendocrine; mix small cell-large cell, 7 neuroendocrine small cell, 8 non-small cell adenocarcinoma, 3 non-small large cell carcinoma, 8 non-small squamous cell carcinoma, 7 pleura mesothelioma), lymphocytes (10 hodgkin's lymphoma), melanocytes (3 malignant melanoma), meninges (8 meningioma, 1 atypical meningioma), mouth (4 squamous cell carcinoma, 1 keratinizing squamous cell carcinoma), nose (4 squamous cell carcinoma, 1 keratinizing squamous cell carcinoma), |

TABLE 1b-continued

Summary of sample types, numbers and histology used for comparing brain tumors to normal brain, non-brain tumors and brain metastases

| N | | Detail |
|---|---|---|
| | | ovary (7 serous papillary cancer), |
| | | pancreas (3 adenocarcinoma, 2 ductal adenocarcinoma, 2 exocrine adenocarcinoma), |
| | | prostate (7 samples including 2 bph samples) |
| | | small intestine (7 stromal tumor, 1 adenocarcinoma), |
| | | stomach adenocarcinoma (5), |
| | | testis seminoma (3), |
| | | thymus thymoma (3 type b2, 4 type b3), |
| | | thyroid (4 carcinoma, 3 papillary carcinoma, 1 papillary tall cell carcinoma), |
| | | tongue (2 squamous cell carcinoma, 8 keratinizing squamous cell carcinoma), |
| 50 | Metastases in brain | bladder (1 transitional cell carcinoma), breast (2 carcinoma, 2 adenocarcinoma, 4 ductal carcinoma, 5 infiltrating ductal carcinoma), colon (5 adenocarcinoma), endometrial tumor (1), kidney (2 clear cell carcinoma, 1 renal cell carcinoma), lung (10 including 1 carcinoma, 1 neuroendocrine small-cell carcinoma, 6 non-small cell adenocarcinoma, 1 non-small squamous cell carcinoma), melanocytes (4 melanoma, 2 malignant melanoma), unknown (3 carcinoma, 5 adenocarcinoma, 1 small cell carcinoma, 2 sarcoma), |

| N | Additional samples in qRT-PCR validation set | Detail |
|---|---|---|
| 15 | Brain primary tumors qRT-PCR validation set | anaplastic oligodendroglioma (1), astrocytoma (5), glioblastoma multiforme (2), oligodendroglioma (7) |
| 8 | Other primary tumors | bladder (1 transitional cell carcinoma), kidney (1 renal cell carcinoma), liver (1 hepatocellular carcinoma), lung (2 including 1 adenocarcinoma, 1 pleura mesothelioma), ovary (1 adenocarcinoma), pancreas (3 adenocarcinoma, 2 ductal adenocarcinoma, 2 exocrine adenocarcinoma), pancreas (1 neuroendocrine carcinoma), thymus thymoma (1 type b2) |
| 10 | Metastases in brain | breast (2 ductal carcinoma), kidney (3 adenocarcinoma), lung (3 including 1 adenocarcinoma, 2 non-small squamous cell carcinoma), ovary (2 adenocarcinoma) |

2. RNA Extraction

Total RNA was extracted from both the frozen and the FFPE tissues. From the frozen tissues, a sample of approximately 0.5 cm$^3$ was used per case. Total RNA was extracted using the miRvana miRNA isolation kit (Ambion) according to the manufacturer's instructions. Briefly, the sample was homogenized in a denaturing lysis solution followed by an acid-phenol:chloroform extraction and purification on a glass-fiber filter.

From the FFPE samples, total RNA was isolated from seven to ten 10-micron-thick tissue sections per case using the miRdictor™ extraction protocol developed at Rosetta Genomics. Briefly, the sample was incubated few times in xylene at 57° C. to remove paraffin excess, followed by ethanol washes. Proteins were degraded by proteinase K solution at 45° C. for few hours. The RNA was extracted with acid phenol:chloroform followed by ethanol precipitation and DNAse digestion. Total RNA quantity and quality was measured by Nanodrop ND-1000 (NanoDrop Technologies, Wilmington, Del.).

3. miRdicator™ Array Platform

Custom microRNA microarrays were produced by printing DNA oligonucleotide probes representing ~650 DNA oligonucleotide probes representing microRNAs (Sanger database, version 9 and additional Rosetta validated and predicted miRNAs). Each probe, printed in triplicate, carries up to 22-nt linker at the 3' end of the microRNA's complement sequence in addition to an amine group used to couple the probes to coated glass slides. 20 μM of each probe were dissolved in 2×SSC+0.0035% SDS and spotted in triplicate on Slide E coated microarray slides (Schott Nexterion, Mainz, Germany) using the BioRobotics MicroGrid II microarrater (Genomic Solutions, Ann Arbor, Mich.) according to the manufacturer's directions. 54 negative control probes were designed using the sense sequences of different microRNAs. Two groups of positive control probes were designed to hybridize to miRdicator™ array (i) synthetic small RNA were spiked to the RNA before labeling to verify the labeling efficiency and (ii) probes for abundant small RNA (e.g. small nuclear RNAs (U43, U49, U24, Z30, U6, U48, U44), 5.8 s and 5 s ribosomal RNA) are spotted on the array to verify RNA quality. The slides were blocked in a solution containing 50 mM ethanolamine, 1M Tris (pH9.0) and 0.1% SDS for 20 min at 50° C., then thoroughly rinsed with water and spun dry.

4. Cy-Dye Labeling of miRNA for Microarray

Up to 5 μg (mean: 4.5 μg) of total RNA were labeled by ligation of an RNA-linker, p-rCrU-Cy/dye (Dharmacon, Lafayette, Colo.), to the 3'-end with Cy3 or Cy5. The labeling reaction contained total RNA, spikes (0.1-20 fmoles), 300 ng RNA-linker-dye, 15% DMSO, 1x ligase buffer and 20 units of T4 RNA ligase (NEB New England Biolabs, Ipswich, Mass.) and proceeded at 4° C. for 1 hr followed by 1 hr at 37° C. The labeled RNA was mixed with 3× hybridization buffer (Ambion, Austin, Tex.), heated to 95° C. for 3 min and than added on top of the miR microarray. Slides were hybridized 12-16 hr in 42° C., followed by two washes in room temperature with 1×SSC and 0.2% SDS and a final wash with 0.1×SSC.

Arrays were scanned using the Agilent DNA Microarray Scanner Bundle (Agilent Technologies, Santa Clara, Calif.) at resolution of 10 μm at 100% power. Array images were analyzed using the SpotReader software (Niles Scientific, Portola Valley, Calif.).

5. Signal Calculation and Normalization of Microarray Data

The initial data set consisted of signals measured for multiple probes for every sample. Triplicate spots were combined to one signal by taking the logarithmic mean of the reliable spots. All data was log-transformed (natural base) and the analysis was performed in log-space. A reference data vector for normalization R was calculated by taking the median expression level for each probe across all samples in each dataset. For each sample data vector S, a 2nd degree polynomial F was found so as to provide the best fit between the sample data and the reference data, such that R≈F(S). Remote data points ("outliers") were not used for fitting the polynomial F. For each probe in the sample (element $S_i$ in the vector S), the normalized value (in log-space) $M_i$ is calculated from the initial value $S_i$ by transforming it with the polynomial function F, so that $M_i$=F($S_i$). Data in FIGS. 1 and 2 was translated back to linear-space by taking the exponent.

6. qRT-PCR

One microgram of total RNA was subjected to polyadenylation reaction as described before (Shi and Chiang, 2005, Biotechniques, 39(4):519-25). Briefly, RNA was incubated in the presence of poly (A) polymerase (PAP) (Takara- 2180A), MnCl$_2$, and ATP for 1 h at 37° C. Reverse transcription was performed on the poly-adenylated product. An oligo-dT primer harboring a consensus sequence (complementary to the reverse primer) was used for reverse transcription reaction. The primer is first annealed to the poly A-RNA and then subjected to a reverse transcription reaction of SuperScript II RT (Invitrogen). The cDNA was then amplified by real-time PCR reaction, using a miRNA-specific forward primer, TaqMan probe and universal reverse primer. The reactions were incubated for 10 min at 95° C. followed by 42 cycles of 95° C. for 15 s and 60° C. for 1 min Normalizing the $C_t$ values (per sample) by the $C_t$ of either U6 snRNA, the $C_t$ of hsa-miR-24, or their average $C_t$, shifted at most one sample from each side in the test-set classification predictions.

7. Data Analysis and Statistics

Normalized expression values for each of the samples of the miRs were calculated. P-values were calculated using two-sided t-test on the logarithm of the signal.

The combined metric "L" was defined as the mean log 2 expression of two microRNAs, L≡[log 2(hsa-miR-141 signal)+log 2(hsa-miR-200c signal)]/2. This metric could be used to identify the non-liver primary tumor samples with near-perfect accuracy. The receiver operating characteristic curve (ROC curve) plots the sensitivity against one minus the specificity, and is a measure of classification performance A random classifier has an area under the curve (AUC) of 0.5, and an optimal classifier with perfect sensitivity and specificity of 100% has an area of 1. The ROC curve of the combination of hsa-miR-141 and hsa-miR-200c has an AUC of 0.999. The decision rule "classify as non-liver when L>10" identified samples as non-liver primary tumors with a sensitivity of 98% and a specificity of 100%, with one pancreatic exocrine adenocarcinoma incorrectly classified as HCC. A more "conservative" cutoff at L=9.5 had a sensitivity of 98% and a specificity of 93% (FIG. 1A), with two HCC samples incorrectly identified as non-HCC primary tumors. The same combined metric had AUC=0.997 in identifying metastatic liver adenocacinoma of a known origin from primary HCC (FIG. 1B), with sensitivity=98% and specificity of 93%. For the qRT-PCR data, $L_{RT}$≡[(hsa-miR-141 normalized $C_t$)+(hsa-miR-200c normalized $C_t$)]/2 had AUC=1.

For comparing GI and non-GI primary tumors, the simple decision rule "classify as GI when the expression of hsa-miR-205 is smaller than half the expression of hsa-miR-194" (FIG. 2A) is accurate in all but one case of a stomach primary tumor that is misclassified as non-GI by this rule. The metric (expression of hsa-miR-205)/(expression of hsa-miR-194) had an AUC of 0.989.

For comparing brain tumors, the combined metric $B_0$ was defined as the summed log 2 expression measured by microarray of hsa-miR-124 and hsa-miR-219-5p: $B_0$≡[log 2(hsa-miR-124 signal)+log 2(hsa-miR-219-5p signal)], and had AUC=1 when used to identify primary brain tumors from other primary tumors, but had AUC=0.8987 when used to identify brain primary tumors from brain metastases. The combined metric $B_1$ was defined as the summed log 2 expression measured by microarray of hsa-miR-9* and hsa-miR-92b: $B_1$≡[log 2(hsa-miR-9* signal)+log 2(hsa-miR-92b signal)], and had AUC=1 when used to identify primary brain tumors from other primary tumors or from brain metastases.

The combined metric $B^{RT}$ was defined as the summed log 2 expression levels measured by qRT-PCR data (the $C_t$ values) of hsa-miR-9 and hsa-miR-92b: $B^{RT}$≡100−[$C_t$(hsa-miR-9)+$C_t$(hsa-miR-92b signal)], had AUC=1 in the training set data and one error in the test-set data when used to identify primary brain tumors from other primary tumors or from brain metastases. The combined metric $B^{RT*}$ was defined as the summed qRT-PCR $C_t$ values of hsa-miR-9* and hsa-miR-92b: $B^{RT*}$≡100−[$C_t$(hsa-miR-9*)+$C_t$(hsa-miR-92b signal)], had AUC=1 in the training set data and one error in the test-set data when used to identify primary brain tumors from other primary tumors or from brain metastases.

TABLE 2 miR and hairpin SEQ ID NOS:

| miR name | MID | HID |
|---|---|---|
| hsa-miR-194 | 1 | 2, 3 |
| hsa-miR-205 | 4 | 5 |
| hsa-miR-141 | 6 | 7 |
| hsa-miR-200c | 8 | 9 |
| hsa-miR-200a | 10 | 11 |
| hsa-miR-200b | 12 | 13 |
| hsa-miR-92b | 14 | 15 |
| hs a-miR-124a | 16 | 17-19 |
| hsa-miR-9* | 20 | 21-23 |
| hsa-miR-219 | 24 | 25-26 |
| hsa-miR-9 | 27 | 21-23 |
| hsa-miR-128a | 28 | 29 |
| hsa-miR-128b | 30 | 31 |
| hsa-miR-122a | 32 | 33 | miR name: is the miRBase registry name (release 9.1).
MID: is the SEQ ID NO of the mature microRNA.
HID: is the SEQ ID NO of the microRNA hairpin precursor (Pre-microRNA).

TABLE 3

Primers and probes SEQ ID NOS:

| Target miR name | Fwd Primer Sequence SEQ ID NO: | MGB probe Sequence SEQ ID NO: | Rev Primer Sequence SEQ ID NO: |
|---|---|---|---|
| hsa-miR-124 | 34 | 39 | 44 |
| hsa-miR-9 | 35 | 40 | |
| hsa-miR-9* | 36 | 41 | |
| hsa-miR-92b | 37 | 42 | |
| U6 | 38 | 43 | |

Example 1

Specific microRNAs are Able to Distinguish Between Primary Non-Hepatic and Hepatic Tumors microRNA expression levels were profiled in 144 tumor samples including 30 primary HCC samples, 63 primary tumors from epithelial origins, 46 liver metastases from epithelial origins, and 5 adenocarcinoma metastases to the liver from unknown origin. The primary HCC samples were compared to the other primary tumors and to the liver metastases samples. Hsa-miR-122a (SEQ ID NO: 32), which is a highly liver-specific microRNA, had the strongest effect when comparing primary HCC tumors to other primary tumors with a fold-change>90, and could identify HCC from other primary tumors (p-value=1.4e-38, AUC=1). However, this microRNA is also found at high levels in the RNA extracted from liver metastases (FIG. 1A), ostensibly due to contamination from the adjacent normal liver tissue, and is not a good marker for identifying liver metastases (fold-change of medians 1.1, p-value=0.28, AUC=0.56). By using high-throughput profiling, the microRNA family of hsa-miR-200a,b,c (SEQ ID NOS: 8, 10 and 12) and hsa-miR-141 (SEQ ID NO: 6) were identified as strongly expressed in primary tumors from epithelial origins of common liver metastases, but are not expressed in liver primary tumors (p-value<1e-11, AUC>0.9 for each). Because these microRNAs are not expressed in the liver background, they are also useful in distinguishing between primary HCC tumors and metastatic tumors to the liver (p-value<1e-11, AUC>0.9 for each). For these microRNAs, unlike hsa-miR-122a, the expression level in the liver metastases is similar to the expression level in the non-HCC primary tumors, in sharp contrast to their expression level in the liver primary tumors (FIG. 1A).

Of this family of microRNAs, the strongest effect was found for hsa-miR-200c and hsa-miR-141 (FIG. 1B). Each of these microRNAs could be used to distinguish between primary HCC tumors and metastatic tumors to the liver with very high accuracy (AUC>0.98). The expression level of these two microRNAs can be combined to create a powerful classifier. The combined metric L is defined as the sum of the logarithm (base 2) of the signals of the two microRNAs, providing robustness to the classifier by adding two signals. A simple decision rule, "classify as HCC if L≤18, classify as non-HCC if L>18", has a sensitivity of 98% in identifying non-HCC samples and a specificity of 93%, with only 4 errors of 144 samples (AUC=0.9980). A more conservative classifier can be defined by allowing a margin for uncertainty, of factor 4 above or below the threshold (equivalent to two cycles in qRT-PCR measurements). The classification rule "classify as HCC if L<16, classify as non-HCC if L>20, leave unidentified if 16≤L≤20" leaves 7 samples of 144 (<5%) unclassified, and correctly classifies all other samples, including 5 cases of metastatic liver adenocarcinoma of unknown origin (FIG. 1B).

Figure 1C:
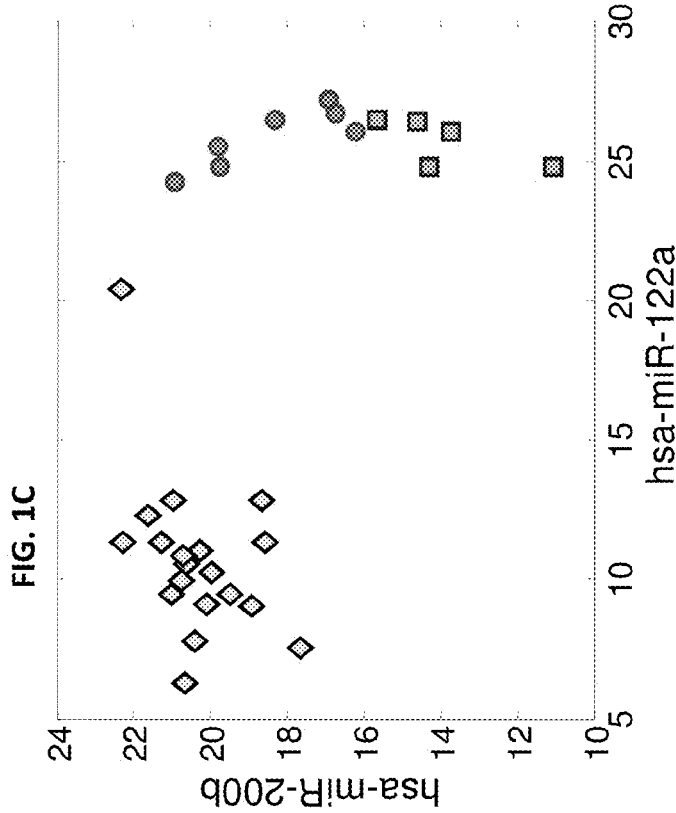
Figure 2A:
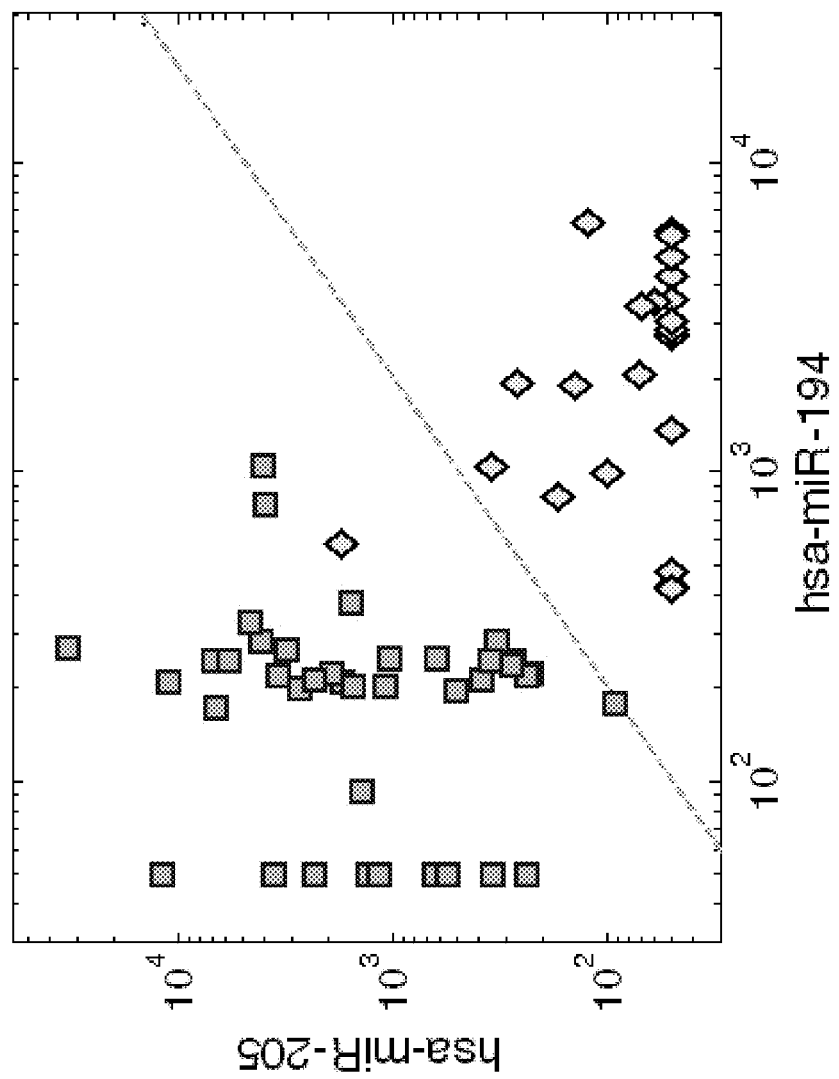
FIGS. 2A and B demonstrate the identification of gastrointestinal tumors and metastases using a combination of two microRNA biomarkers.

These findings were validated by qRT-PCR, measuring the expression levels of these microRNAs in 31 samples including 24 new samples. The qRT-PCR data showed an identical pattern, with hsa-miR-122a high in all samples from the liver (FIG. 1C), and the miR-200 family specifically high in samples of non-liver origin (FIG. 1C). Again, a simple combination of hsa-miR-200c and hsa-miR-141 could identify primary from metastatic liver tumors with near-perfect accuracy (FIG. 1D).

Figure 3A:
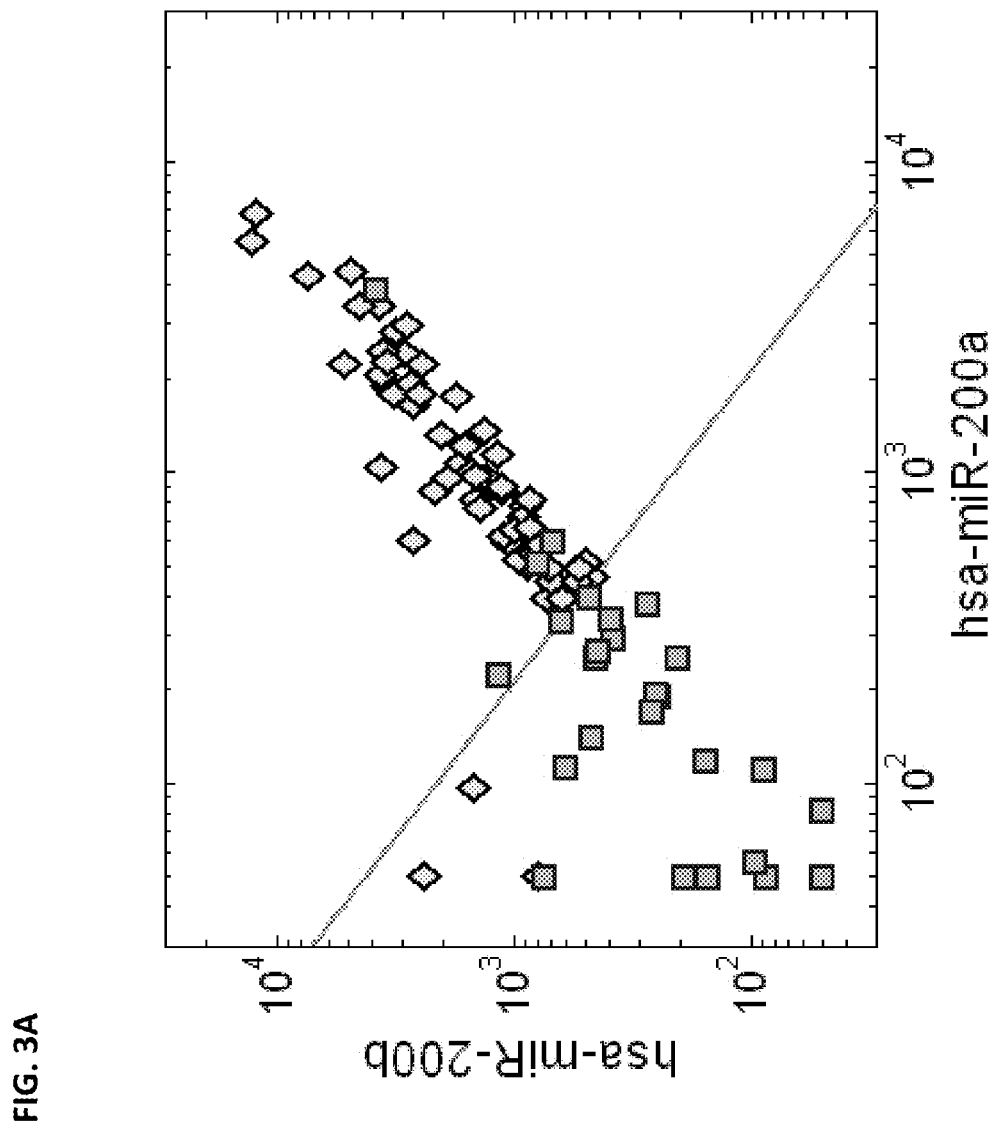
FIGS. 3A and B demonstrate the identification of non-HCC epithelial tumor samples and metastases using a combination of two microRNA biomarkers.
Figure 3B:
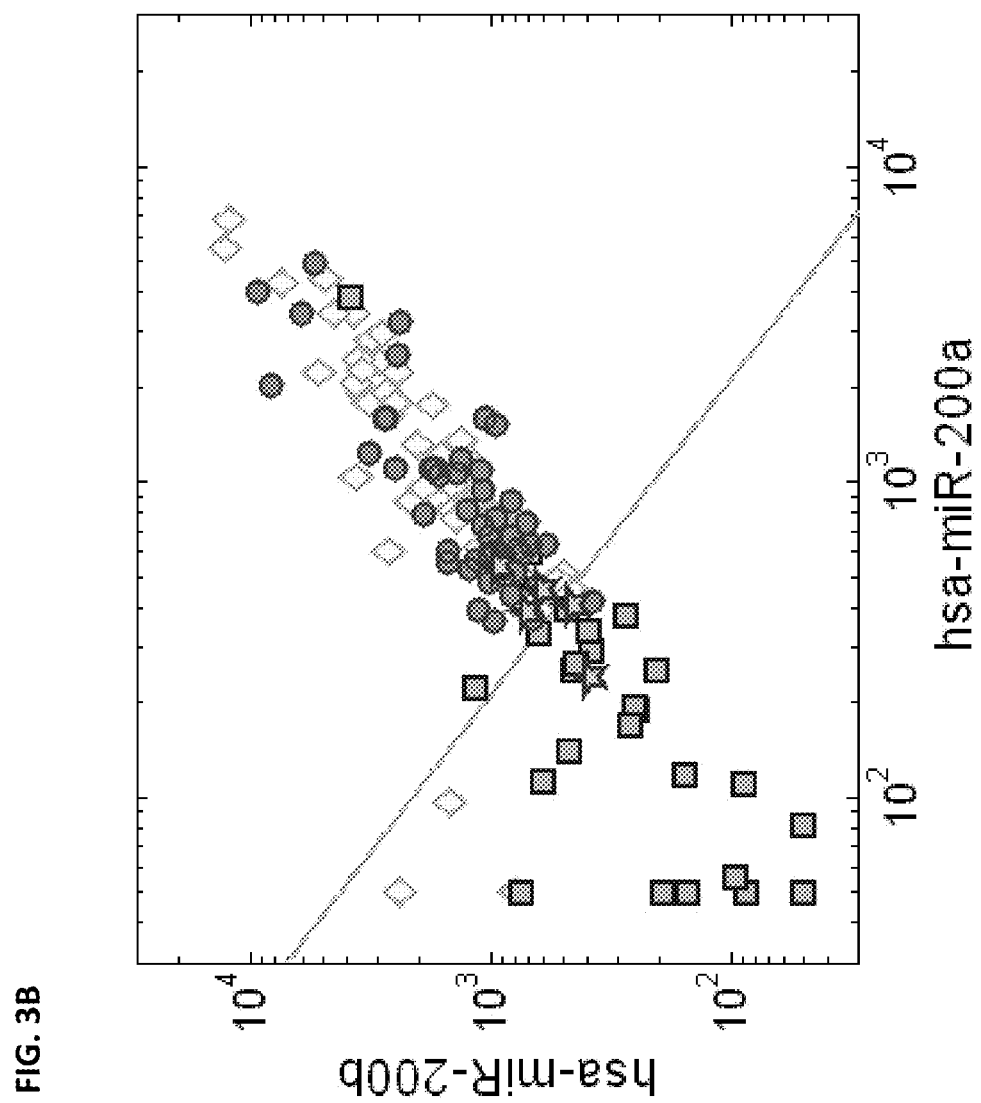
FIG. 3B. Expression levels of hsa-miR-200a and hsa-miR-200b in 46 samples of adenocarcinoma metastases to the liver of known origin (circles) and 5 samples of adenocarcinoma metastases to the liver of unknown origin (stars). The gray line marks Cab=17.7. Only three adenocarcinoma metastases samples (one from breast cancer origin and two from unknown origin) have Cab<17.7.

Similar results were obtained by using the combination of hsa-miR-200a (SEQ ID NO: 10) and hsa-miR-200b (SEQ ID NO: 12) (FIG. 3A-B, p-value<$2*10^{-12}$ for each comparing hepatocellular carcinoma samples to non-hepatic primary tumor samples or to metastatic liver adenocacinoma of a known origin or to both together).

TABLE 4 microRNA expression in HCC primary tumors compared to their expression in other primary tumors and metastases, from microarray data.

| | HCC primary liver tumors vs.: | | | | | | | | |
|---|---|---|---|---|---|---|---|---|---|
| | Compared to other primary tumors | | | Compared to metastases in liver | | | Compared to both other primary and metastases | | |
| microRNA or metric: | p-value[†] | fold-chng[‡] | AUC | p-value[†] | fold-chng[‡] | AUC | p-value[†] | fold-chng[‡] | AUC |
| hsa-miR-122[‡] | 1.4E−38 | 91.1 | 1.0000 | 2.8E−01 | 1.1 | 0.5623 | 6.3E−09 | 56.7 | 0.8193 |
| hsa-miR-200a | 4.8E−13 | 1/5.7 | 0.9185 | 7.3E−14 | 1/4.8 | 0.9492 | 1.3E−17 | 1/5.1 | 0.9277 |
| hsa-miR-200b | 1.5E−15 | 1/5.7 | 0.9339 | 1.9E−12 | 1/4.3 | 0.9297 | 2.7E−19 | 1/4.6 | 0.9249 |
| hsa-miR-200c | 1.7E−34 | 1/25 | 0.9947 | 8.9E−27 | 1/23 | 0.9877 | 1.0E−46 | 1/25 | 0.9921 |
| hsa-miR-141 | 1.7E−39 | 1/44 | 0.9979 | 1.2E−27 | 1/27 | 0.9905 | 1.5E−48 | 1/35 | 0.9950 |
| L[†] | 5.7E−38 | 1/989 | 0.9984 | 4.2E−29 | 1/627 | 0.9971 | 2.1E−50 | 1/866 | 0.9980 |

[†]P-values are calculated on log-signal of microRNA expression, measure by microarray, and on L which is in log-space (methods).
[‡]"fold-chng" is the fold change, calculated by the median signal in HCC divided by the median signal in other tissues. For hsa-miR-122a, fold change is greater than 1 indicating a higher expression in HCC. For all other rows, signal is lower in HCC.

TABLE 5 microRNA expression in HCC primary tumors compared to their expression in other primary tumors and metastases, from qRT-PCR data.

| | HCC primary liver tumors vs.: | | | | | | | | |
|---|---|---|---|---|---|---|---|---|---|
| | Compared to other primary tumors | | | Compared to metastases in liver | | | Compared to both other primary and metastases | | |
| microRNA or metric: | p-value[†] | fold-chng[‡] | AUC | p-value[†] | fold-chng[‡] | AUC | p-value[†] | fold-chng[‡] | AUC |
| hsa-miR-122[‡] | 1.5E−10 | 5E+4 | 1.0000 | 8.3E−01 | 1.0 | 0.4857 | 2.6E−03 | 3E+4 | 0.8615 |
| hsa-miR-200a | 4.4E−09 | 1/883 | 1.0000 | 5.3E−03 | 1/89 | 0.9286 | 8.1E−07 | 1/542 | 0.9808 |
| hsa-miR-200b | 2.5E−09 | 1/80 | 1.0000 | 1.5E−03 | 1/16 | 1.0000 | 4.0E−08 | 1/60 | 1.0000 |

TABLE 5-continued microRNA expression in HCC primary tumors compared to their expression in other primary tumors and metastases, from qRT-PCR data.

| | HCC primary liver tumors vs.: | | | | | | | | |
|---|---|---|---|---|---|---|---|---|---|
| | Compared to other primary tumors | | | Compared to metastases in liver | | | Compared to both other primary and metastases | | |
| microRNA or metric: | p-value[†] | fold-chng[‡] | AUC | p-value[†] | fold-chng[‡] | AUC | p-value[†] | fold-chng[‡] | AUC |
| hsa-miR-200c | 9.9E−14 | 1/643 | 1.0000 | 3.5E−05 | 1/678 | 1.0000 | 1.2E−12 | 1/661 | 1.0000 |
| hsa-miR-141 | 2.3E−11 | 1/323 | 1.0000 | 5.7E−04 | 1/164 | 1.0000 | 8.1E−10 | 1/305 | 1.0000 |
| $L_{RT}$[†] | 3.0E−13 | 1/319 | 1.0000 | 1.1E−04 | 1/230 | 1.0000 | 1.2E−11 | 1/279 | 1.0000 |

[†]P-values are calculated on normalized $C_t$ values of microRNA expression by qRT-PCR, and $L_{RT}$, which is the average $C_t$ of hsa-miR-200c and hsa-miR-141 (see methods).
[‡]"fold-chng" is the fold change, calculated by the median signal ($2^{C_t}$) in HCC divided by the median signal ($2^{C_t}$) in other tissues. For hsa-miR-122a, fold change is greater than 1 indicating a higher expression in HCC. For all other rows, signal is lower in HCC.

Example 2

Figure 2B:
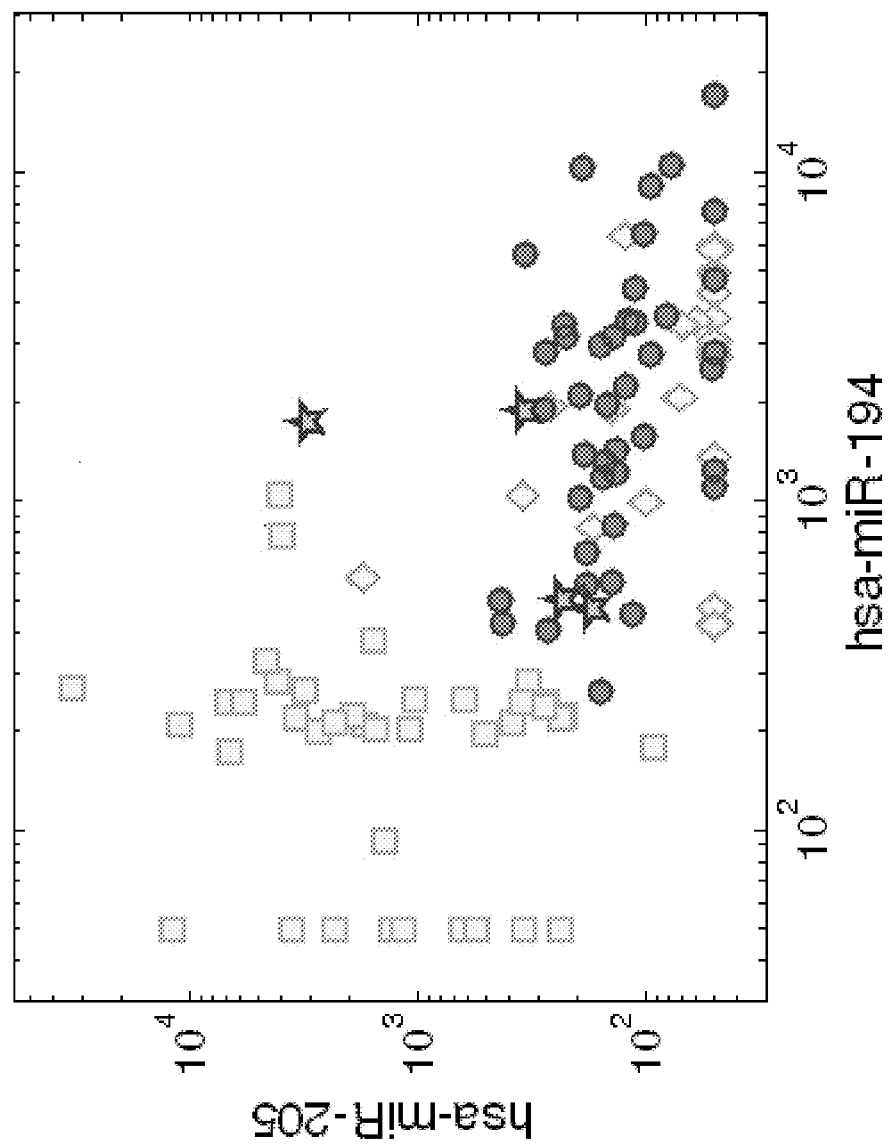
FIG. 2B. Expression levels of hsa-miR-194 and hsa-miR-205 in 42 samples of liver metastases from GI origin (circles) and 4 metastases to the liver of non-GI origin (stars).

Specific microRNAs are Able to Distinguish Between Primary GI Tumors and Non-GI Primary Tumors The microRNA expression can provide further information on the possible origin of liver metastases. Another pair of microRNAs, hsa-miR-194 (SEQ ID NO: 1) and hsa-miR-205 (SEQ ID NO: 4), had significant different expression (p-value<1e-12 for each) in primary tumors from gastrointestinal (GI) origin (14 colon, 5 pancreas, 5 stomach) compared to primary tumors of non-GI epithelial origin (24 lung, 15 breast). The ratio of these expression levels could be used to accurately identify primary tumors from non-GI origin: the decision rule "classify as non-GI primary when the expression of hsa-miR-205 is greater than half the expression of hsa-miR-194" (FIG. 2A; dashed line marks the decision boundary) had a sensitivity of 100% and specificity of 96% (AUC=0.9893). In the liver metastases, despite the small number of samples, this trend was maintained (FIG. 2B). However, since hsa-miR-194 is also highly expressed in liver tissue, the contamination of these metastases by the surrounding liver tissue raised significantly the expression of hsa-miR-194, and thereby reduced the significance of its differential expression (p-value=0.0011 for hsa-miR-205, but only p-value=0.15 for hsa-miR-194). Nevertheless, a very high ratio of expression of hsa-miR-194 to hsa-miR-205 is observed only in metastases of GI origin and can thus be used for their identification (AUC=0.8988).

Example 3

Figure 4A:
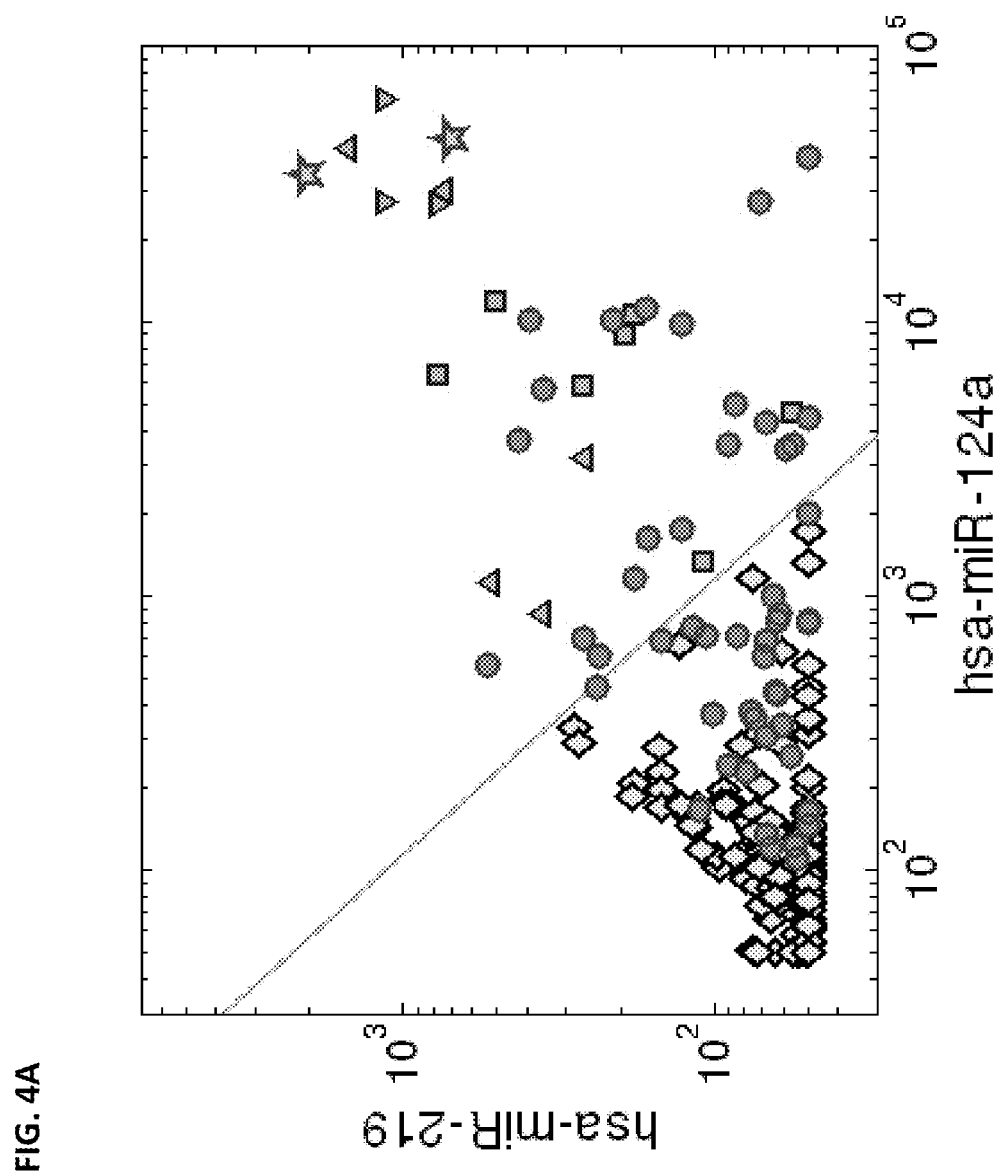
FIGS. 4A and B demonstrate the identification of metastatic brain tumors using microRNA microarray data.
Figure 5A:
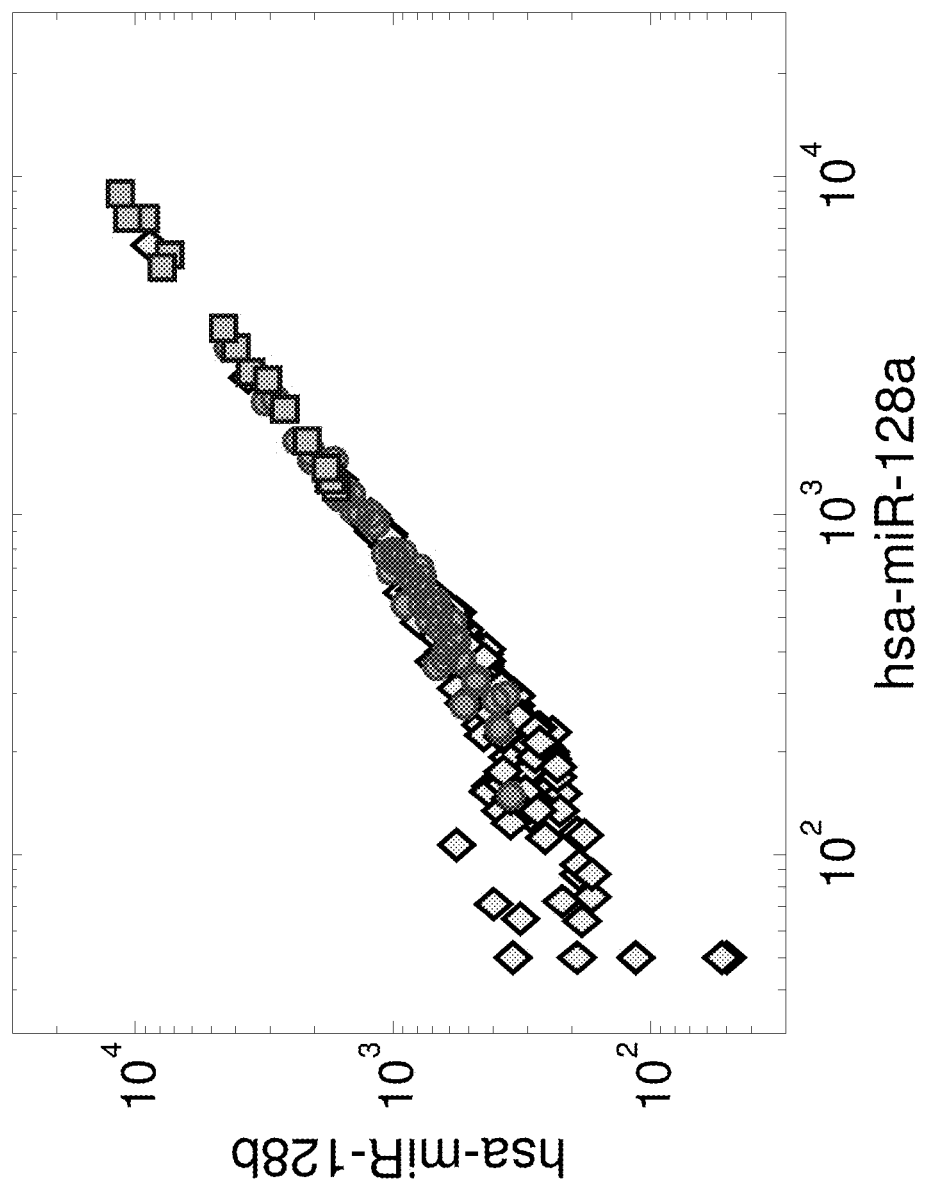
FIGS. 5A and B demonstrate the expression levels of microRNA as detected by microarray in 15 primary brain tumors (squares), 187 primary tumors from other tissues (diamonds), and 50 brain metastases from various tissue origins (circles).
Figure 5B:
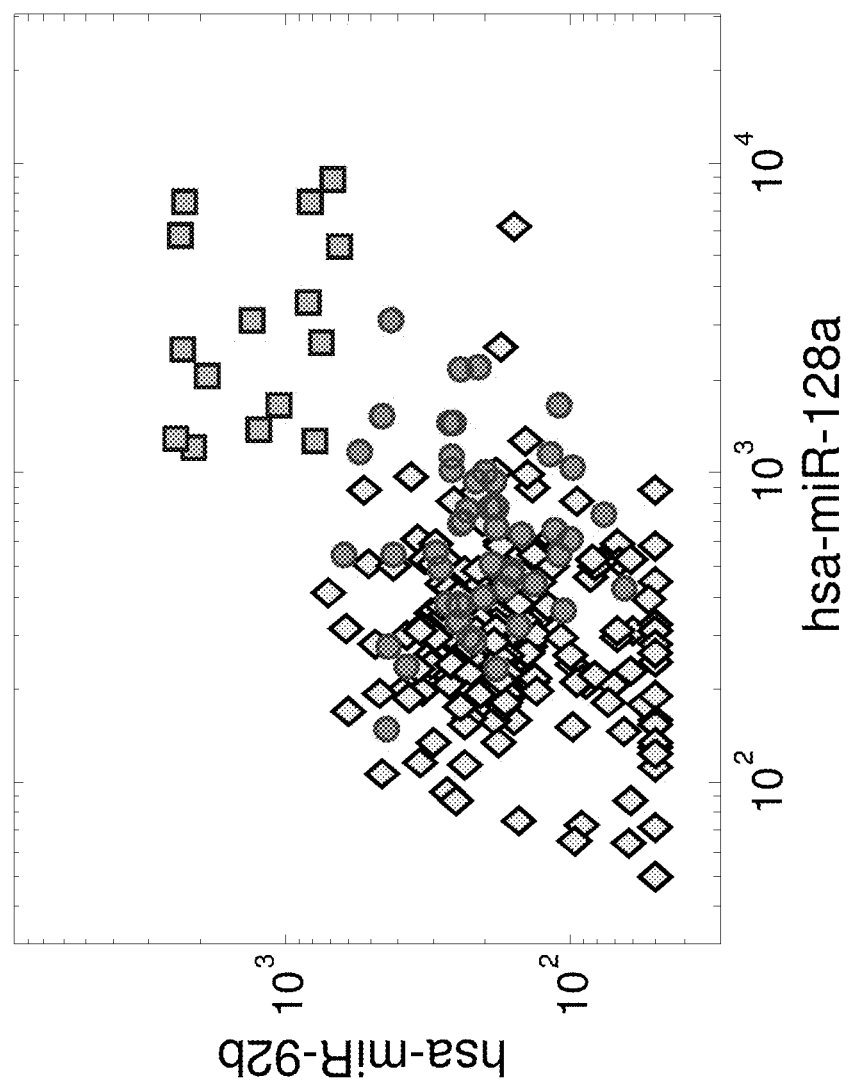
FIG. 5B. In contrast to hsa-miR-128a, hsa-miR-92b (SEQ ID NO: 14) is specifically expressed in brain primary tumors, and is lower in primary tumors from other tissues and in their brain metastases.

Specific microRNAs are Able to Distinguish Between Primary Brain Tumors, Brain Metastases, Non-Brain Primary Tumors and Normal Brain Samples microRNA expression levels were profiled on a microarray platform in 252 tumor samples including 15 brain primary tumor samples, 187 non-brain primary tumors, 50 brain metastases from various tissue origins and 2 normal brain samples. The brain primary tumor samples were compared to the other primary tumor samples, to normal brain samples and to samples of brain-located metastases (Table 6). Hsa-miR-124 (SEQ ID NO: 16), which is highly specific to the nervous system, displayed the greatest disparity in expression when comparing brain primary tumors to other primary tumors, with a fold-change of ~100 (p-value=5.1e-57, AUC=0.9976, see Table 6). A combination of hsa-miR-124 and hsa-miR-219 (SEQ ID NO: 24) ($B_0$, see methods) could be used to distinguish brain primary tumors from non-brain primary tumors with 100% accuracy (FIG. 4A). Other brain-specific microRNAs such as hsa-miR-128a (SEQ ID NO: 28) and hsa-miR-128b (SEQ ID NO: 30) also showed very strong differential expression between brain primary tumors and other primary tumors (p-value<4e-28, AUC=0.9932, see FIG. 5A). However, these four microRNAs are highly expressed in normal brain and are also found at high levels in RNA extracted from brain metastases (FIG. 4A). This latter effect, ostensibly due to contamination from the adjacent normal brain tissue, limits the utility of these microRNAs to serve as biomarkers for differentiating between brain primary tumors and brain-located metastases (AUC of 0.85~0.95, see Table 6).

Figure 4B:
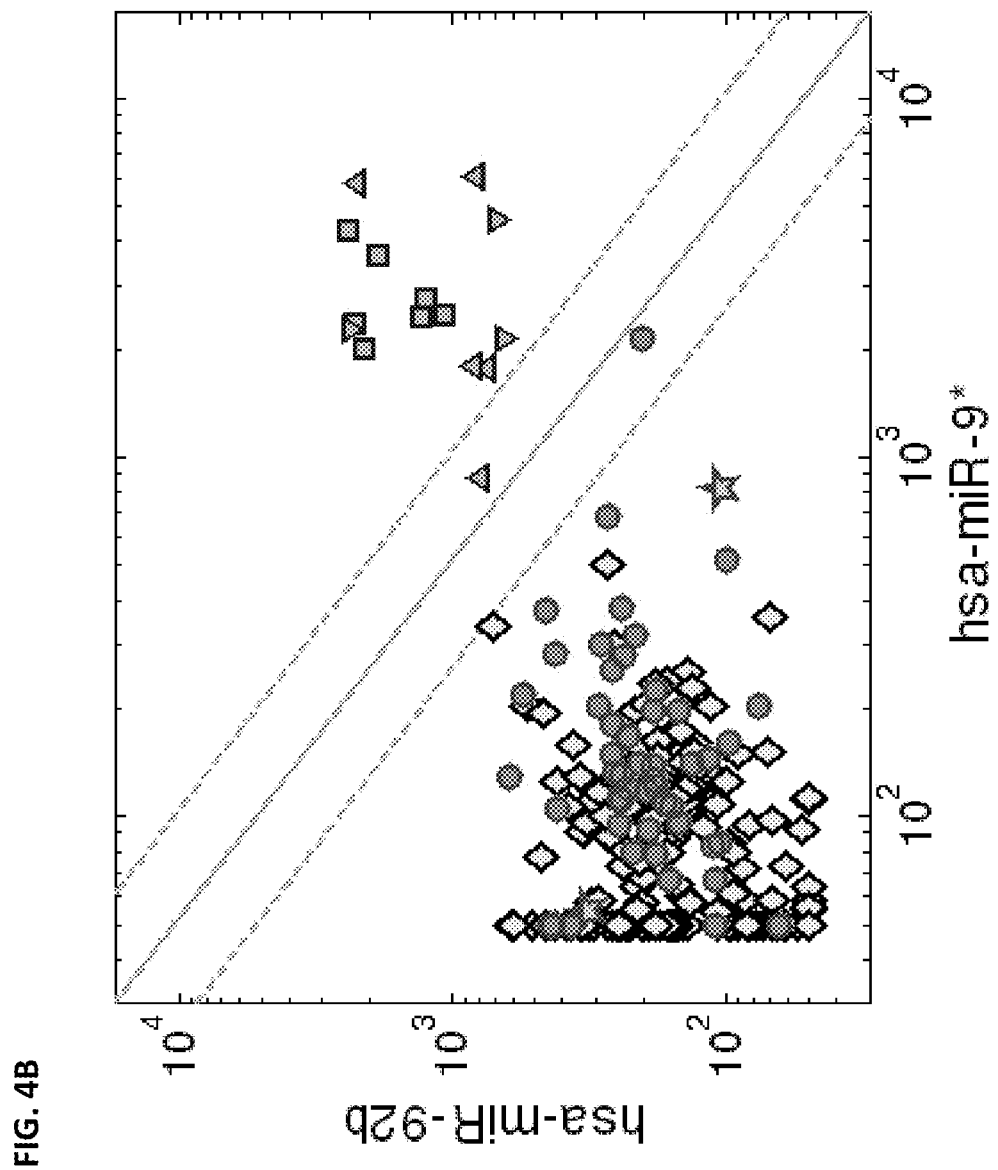
FIG. 4B. Expression levels of hsa-miR-9* (SEQ ID NO: 20) and hsa-miR-92b (SEQ ID NO: 14) in the same samples. Expression levels of these microRNAs are high in brain primary tumors but are low in all other samples. The solid line marks the line where $C_1 \equiv [\log 2(\text{hsa-miR-9*}) + \log 2(\text{hsa-miR-92b})] = 19$, and provides perfect separation between brain primary tumors and other samples, including other primary tumors and metastases to the brain. The dashed lines mark a confidence range of factor 2 above or below, $C_1 = 20$ (upper line) and $C_1 = 18$ (lower line). Only 2 of the samples (<1%) fall within the low-confidence range.

In addition to the aforementioned four microRNAs (hsa-miR-124, hsa-miR-219-5p, hsa-miR-128a and hsa-miR-128b) hsa-miR-9* (SEQ ID NO: 20) and hsa-miR-92b (SEQ ID NO: 14) are expressed specifically in brain tumors and not expressed in other tumor types (FIG. 4B, AUC>0.99) Importantly, these two microRNAs also differentiate accurately between brain primary tumors and metastatic tumors located in the brain (p-value<3e-18, AUC>0.99 for each) or normal brain samples. Indeed, using a combination of hsa-miR-9* and hsa-miR-92b expression ($B_1$, see methods) it is possible to distinguish brain primary tumor samples from all other samples with 100% accuracy in the microarray data (FIG. 4B). A simple decision rule, "classify as primary brain tumor if $B_1>19$, classify as other if $B_1 \leq 19$", identifies correctly all samples. A more conservative classifier can be defined by allowing a margin for uncertainty of factor 2 above or below the threshold (equivalent to one cycle in qRT-PCR measurements). The classification rule "classify as brain primary if $B_1>20$, classify as other if $B_1<18$, leave unidentified if $18 \leq B_1 \leq 20$" leaves only 2 samples out of 252 (<1%) as unclassified (FIG. 4B), and classifies correctly all other samples.

Figure 6A:
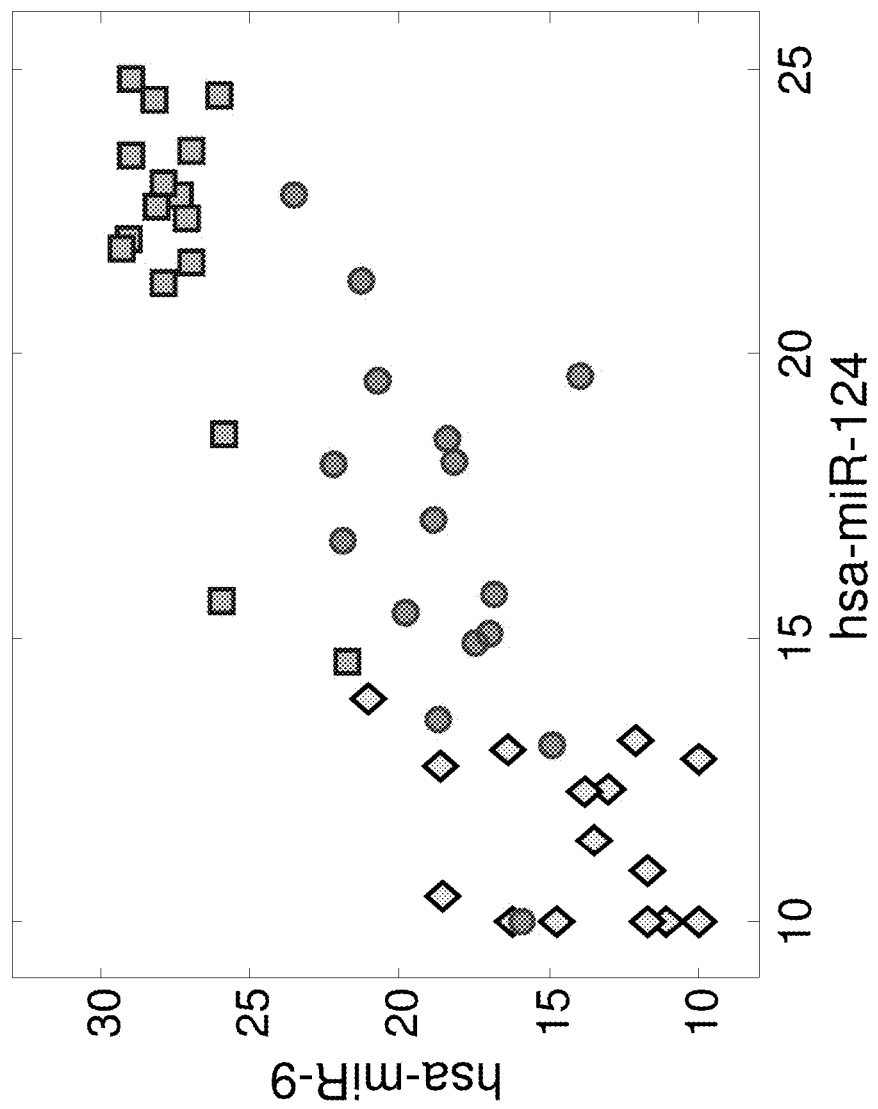
FIGS. 6A and B demonstrate the identification of metastatic brain tumors using microRNA qRT-PCR data.

To validate these findings, 14 of these samples and 33 additional samples were profiled by qRT-PCR, for four potential biomarkers: hsa-miR-124, hsa-miR-9, hsa-miR-9* and hsa-miR-92b (Table 7), and two controls: hsa-miR-24, which was found to be relatively constantly expressed in the microarray data, and snRNA U6. These microRNAs showed the same pattern as observed in the microarray data (Table 7). Hsa-miR-124 showed strong expression in the brain primary tumors, weak expression in other primary tumors, and intermediate expression in the metastases (FIG. 6A).

Figure 6B:
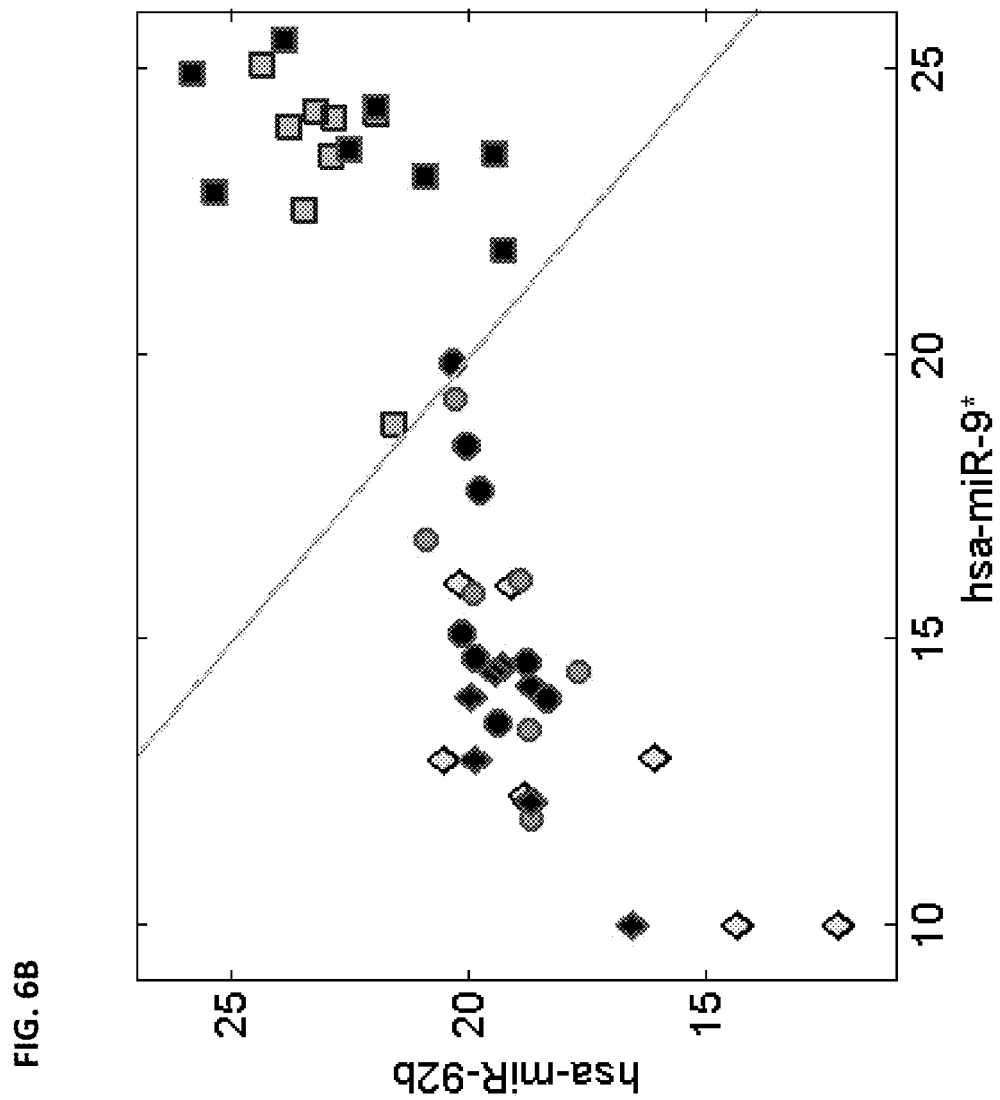
FIG. 6B. Expression levels (50-$C_t$) of hsa-miR-9* (SEQ ID NO: 20) and hsa-miR-92b (SEQ ID NO: 14) in the same samples. Expression levels of these microRNAs are high in brain primary tumors and lower in all other samples. The solid line marks $C^{RT*} \equiv 100 - [C_t(\text{hsa-miR-9*}) + C_t(\text{hsa-miR-92b})] = 39.9$, a threshold which was fit to the training set half of the data. The test-set samples (dark squares/circles/diamonds) were accurately classified by this threshold, with one outlier. Data points with $C_t$ larger than 40 are shown with $C_t = 40$, at (50-$C_t$)=10.

Thus, hsa-miR-124 was not a good candidate for identifying metastatic tumors to the brain. On the other hand, hsa-miR-9 (SEQ ID NO: 27), hsa-miR-9* (SEQ ID NO: 20), and hsa-miR-92b (SEQ ID NO: 14) showed specific strong expression in primary brain tumors with lower expression in other tumors and in metastases to the brain (FIG. 6), with significant differences and strong separability between brain primary tumors and brain metastases (Table 7).

Combinations of hsa-miR-92b with either hsa-miR-9 ($B^{RT}$) or with hsa-miR-9* ($B^{RT*}$) were defined by summing their qRT-PCR $C_t$ values (see Methods). A threshold was selected for classification for each combination using half of the samples as a training set. The classification accuracy was then tested on the second half of the data set which was used as a test set. The classifications on the test set were near perfect with one outlier of 23 samples, reaching 100% accuracy in identifying non-brain primary tumors from brain primary tumors, and 88% sensitivity with 100% specificity in identifying metastatic brain tumors from brain primary tumors, for both $B^{RT}$ (FIG. 6B) and $B^{RT*}$. Indeed, these combinations show significant differences in expression that can be used to classify primary from metastatic brain tumors (Table 7).

Based on these data, it is proposed that hsa-miR-9/9* and hsa-miR-92b, and their combination, represent new bio-markers that can be used to classify brain malignancies—primary versus secondary.

The gene encoding hsa-miR-9/9* appears in the human genome in three places, in chromosomes 1, 5, and 14, each an identical copy. Hsa-miR-92b is found on chromosome 1 and differs by only one nucleotide in its first 20 from hsa-miR-92a, a member of the oncogenic miR-17-92 cluster. However, the expression patterns of hsa-miR-92a correlates only very weakly with that of and hsa-miR-92b and does not enable classification of brain malignancies (Table 6).

TABLE 6

Comparison between microRNA expression in primary brain tumors and expression in other primary tumors or expression in brain metastases, based on microRNA microarray data

| | Primary brain vs. | | | | | |
| --- | --- | --- | --- | --- | --- | --- |
| | Other primary tumors | | | Brain metastases | | |
| microRNA or metric: | p-value† | fold-chng‡ | AUC | p-value† | fold-chng‡ | AUC |
| hsa-miR-124 | 1.4E−54 | 97.1 | 0.9975 | 5.4E−06 | 12.6 | 0.8600 |
| hsa-miR-219-5p | 9.7E−43 | 10.0 | 0.9679 | 4.1E−09 | 6.9 | 0.8840 |
| $B_0$† | 1.8E−49 | 293.0 | 1.0000 | 9.0E−09 | 27.7 | 0.8987 |
| hsa-miR-128a | 5.4E−27 | 9.3 | 0.9929 | 4.5E−11 | 4.2 | 0.9507 |
| hsa-miR-128b | 4.6E−31 | 9.0 | 0.9932 | 1.7E−11 | 4.5 | 0.9520 |
| hsa-miR-9* | 1.4E−64 | 31.3 | 1.0000 | 9.1E−22 | 18.9 | 0.9933 |

TABLE 6-continued

Comparison between microRNA expression in primary brain tumors and expression in other primary tumors or expression in brain metastases, based on microRNA microarray data

| | Primary brain vs. | | | | | |
| --- | --- | --- | --- | --- | --- | --- |
| | Other primary tumors | | | Brain metastases | | |
| microRNA or metric: | p-value† | fold-chng‡ | AUC | p-value† | fold-chng‡ | AUC |
| hsa-miR-92b | 1.8E−26 | 7.3 | 0.9993 | 2.1E−18 | 5.8 | 1.0000 |
| $B_1$† | 1.7E−57 | 205.9 | 1.0000 | 3.3E−26 | 128.7 | 1.0000 |

See Material and Methods for definitions.
†P-values are calculated on log-signal of microRNAs, and on $B_0$ and $B_1$, which are in log-space. Less that 1000 probes were tested, and even after the more severe Bonferroni correction (multiplying each p-value by ~1000), the p-values remain highly significant.
‡"fold-chng" is the fold change, calculated by dividing the median signal in brain primary tumors by the median signal in other tissues.

TABLE 7

Comparison between microRNA expression in primary brain tumors and expression in other primary tumors or expression in brain metastases, based on microRNA qRT-PCR data.

| | Primary brain vs. | | | | | |
| --- | --- | --- | --- | --- | --- | --- |
| | Other primary tumors | | | Brain metastases | | |
| microRNA or metric: | p-value† | fold-chng‡ | AUC | p-value† | fold-chng‡ | AUC |
| hsa-miR-124 | 4.7E−9 | 2144 | 1.0000 | 1.4E−4 | 48 | 0.8633 |
| hsa-miR-9 | 2.3E−11 | 17648 | 1.0000 | 2.0E−11 | 543 | 0.9833 |
| hsa-miR-9* | 1.5E−11 | 1887 | 1.0000 | 1.4E−12 | 415 | 0.9922 |
| hsa-miR-92b | 1.7E−6 | 16 | 0.9542 | 7.2E−7 | 8 | 0.9219 |
| $B^{RT}$ | 1.1E−10 | 2.9E+5 | 1.0000 | 7.7E−12 | 9993 | 0.9961 |
| $B^{RT*}$ | 2.8E−10 | 11868 | 1.0000 | 6.4E−12 | 2428 | 1.0000 |

†P-values are calculated on measured Ct values and on $B^{RT}$ and $B^{RT*}$, which are in log-space. Here only the listed 4 potential biomarkers and two combinations were tested, and no correction for multiple hypothesis testing is needed.
‡"fold-chng" is the fold change, calculated by converting the data to linear space (by taking the exponent base 2) and dividing the median signal in brain primary tumors by the median signal in other tissues.

The foregoing description of the specific embodiments so fully reveals the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It should be understood that the detailed description and specific examples, while indicating preferred embodiments of the invention, are given by way of illustration only, since various changes and modifications within the spirit and scope of the invention will become apparent to those skilled in the art from this detailed description.

What is claimed is:

1. A method of distinguishing between a primary gastrointestinal (GI) tumor and a GI metastatic tumor, the method comprising:
   (a) providing RNA from a biological sample obtained from a human subject;
   (b) determining an expression profile of nucleic acids consisting of SEQ ID NOS: 1 and 4, by contacting the RNA with probes consisting of (i) a first nucleic acid probe, wherein the sequence of the first nucleic acid probe consists of the complement of SEQ ID NO: 1 and a linker of 10-60 nucleotides on the 3' end of the complement of SEQ ID NO: 1; (ii) a second nucleic acid probe, wherein the sequence of the second nucleic acid probe consists of the complement of SEQ ID NO: 4 and a linker of 10-60 nucleotides at the 3' end of the complement of SEQ ID NO: 4; and (iii) optionally a control probe; wherein the probes are attached to a solid support;
   (c) comparing the expression profile from the biological sample to a reference expression profile; and
   (d) distinguishing the biological sample as a primary GI tumor or a GI metastatic tumor based on the comparison of the expression profiles.

2. The method of claim 1, wherein an expression level of SEQ ID NO: 4 that is less than or equal to half the expression level of SEQ ID NO: 1 is indicative of a primary GI tumor, and wherein an expression level of SEQ ID NO: 4 that is greater than half the expression level of SEQ ID NO: 1 is indicative of a GI metastatic tumor.

3. The method of claim 1, wherein the primary GI tumor is selected from the group consisting of colon, pancreas and stomach tumor.

4. The method of claim 1, wherein the biological sample is selected from the group consisting of bodily fluid, a cell line and a tissue sample.

5. The method of claim 4, wherein the tissue sample is a fresh, frozen, fixed, wax-embedded or formalin fixed paraffin-embedded (FFPE) tissue.

6. The method of claim 1, wherein the solid substrate comprises a biochip array.

7. The method of claim 1, wherein the expression profile is determined by real-time PCR.

8. The method of claim 7, wherein the real-time PCR further comprises contacting the RNA with a forward primer and a reverse primer.

* * * * *